United States Patent
Brinkley

(10) Patent No.: US 11,547,599 B2
(45) Date of Patent: Jan. 10, 2023

(54) URINARY CATHETER BRIDGING DEVICE, SYSTEMS AND METHODS THEREOF

(71) Applicant: C. R. Bard, Inc., Franklin Lakes, NJ (US)

(72) Inventor: Micah Brinkley, St. Augustine, FL (US)

(*) Notice: Subject to any disclaimer, the term of this patent is extended or adjusted under 35 U.S.C. 154(b) by 115 days.

(21) Appl. No.: 16/640,690

(22) PCT Filed: Sep. 18, 2018

(86) PCT No.: PCT/US2018/051550
§ 371 (c)(1),
(2) Date: Feb. 20, 2020

(87) PCT Pub. No.: WO2019/060309
PCT Pub. Date: Mar. 28, 2019

(65) Prior Publication Data
US 2020/0352775 A1 Nov. 12, 2020

Related U.S. Application Data

(60) Provisional application No. 62/560,513, filed on Sep. 19, 2017.

(51) Int. Cl.
*A61F 5/44* (2006.01)
*A61F 5/453* (2006.01)
*A61M 25/02* (2006.01)

(52) U.S. Cl.
CPC ............ *A61F 5/453* (2013.01); *A61F 5/4408* (2013.01); *A61M 25/02* (2013.01); *A61M 2025/026* (2013.01); *A61M 2205/583* (2013.01)

(58) Field of Classification Search
CPC .......... A61F 5/44; A61F 5/4408; A61F 5/453; A61M 2205/583; A61M 25/02; A61M 5/1418
See application file for complete search history.

(56) References Cited

U.S. PATENT DOCUMENTS

| 480,911 A | 8/1892 | Vance |
| 822,092 A | 5/1906 | Woodruff |

(Continued)

FOREIGN PATENT DOCUMENTS

| CA | 763930 A | 7/1967 |
| CN | 2139835 Y | 8/1993 |

(Continued)

OTHER PUBLICATIONS

U.S. Appl. No. 13/682,420, filed Nov. 20, 2012 Final Office Action dated Jul. 15, 2014.

(Continued)

*Primary Examiner* — Deanna K Hall
(74) *Attorney, Agent, or Firm* — Rutan & Tucker LLP

(57) ABSTRACT

Provided herein is a bridging device including, in some embodiments, a piece of tubing including a securement loop, a first connector at a first end of the piece of tubing, and a second connector at a second end of the piece of tubing. Also provided herein is a male external catheter ("MEC") kit including, in some embodiments, an MEC; a drainage bag for the MEC; and the bridging device for fluidly connecting the MEC to the drainage bag. The securement loop of the piece of tubing is configured for securing the bridging device in a securement device optionally included in the MEC kit. The first connector is configured to connect to the MEC. The second connector is configured to connect to the drainage bag for the MEC. Methods for making and using the foregoing bridging device and MEC kit are also provided.

20 Claims, 5 Drawing Sheets

(56) References Cited

U.S. PATENT DOCUMENTS

Figure 1:
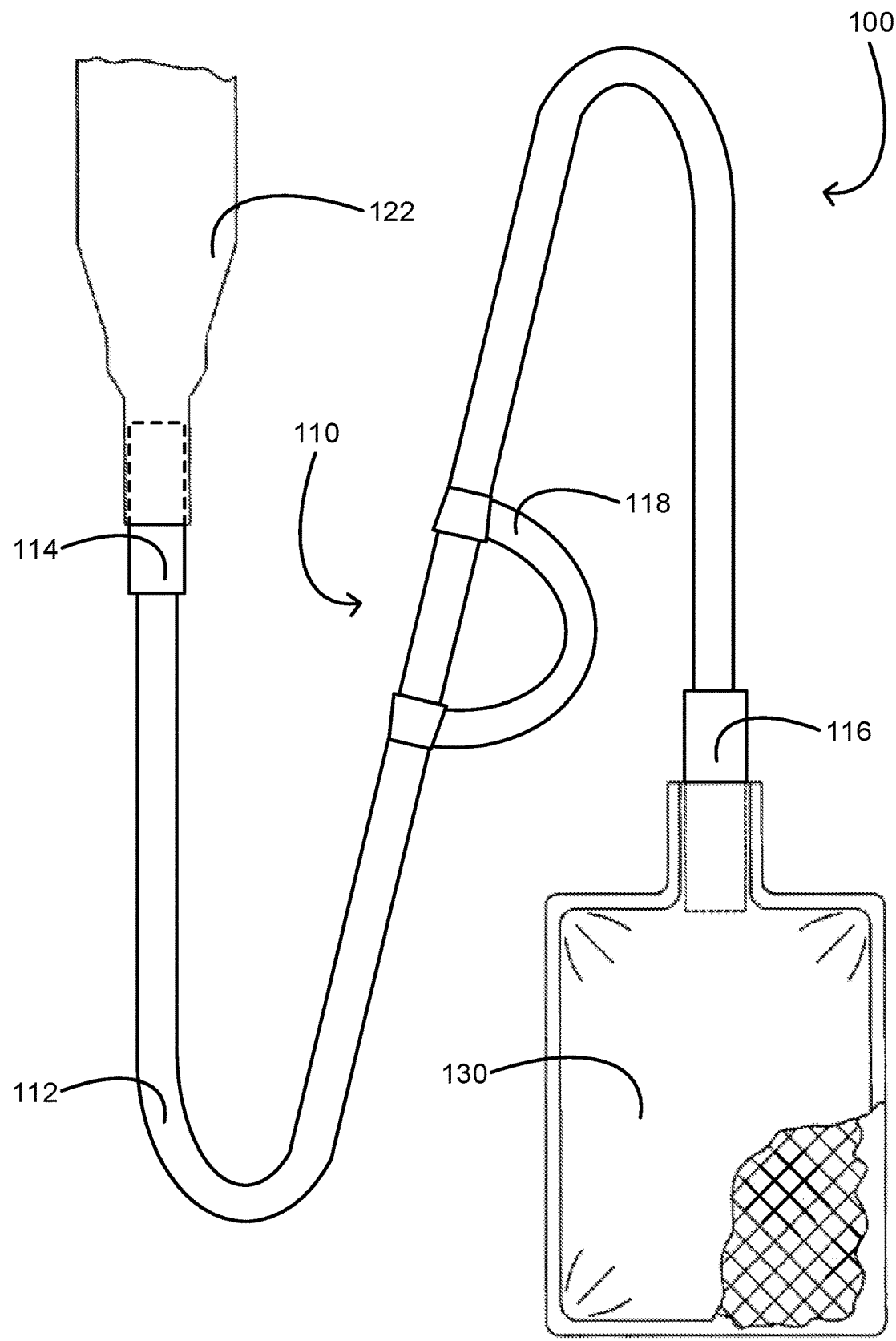

| | | |
|---|---|---|
| 1,235,142 A | 7/1917 | Ichilian |
| 1,643,289 A | 9/1927 | Peglay |
| 1,661,494 A | 3/1928 | Nielsen |
| 2,043,630 A | 6/1936 | Raiche |
| 2,213,210 A | 9/1940 | Egbert |
| 2,228,992 A | 1/1941 | Fry |
| 2,230,226 A | 2/1941 | Auzin |
| 2,248,934 A | 7/1941 | Auzin |
| 2,285,502 A | 6/1942 | Dreyfus |
| 2,308,484 A | 1/1943 | Auzin et al. |
| 2,314,262 A | 3/1943 | Winder |
| 2,320,157 A | 5/1943 | Raiche |
| 2,322,858 A | 6/1943 | Limbert et al. |
| 2,330,399 A | 9/1943 | Winder |
| 2,330,400 A | 9/1943 | Winder |
| 2,389,831 A | 11/1945 | Welsh |
| 2,390,070 A | 12/1945 | Auzin |
| 2,481,488 A | 9/1949 | Auzin |
| 2,494,393 A | 1/1950 | Lamson |
| 2,610,626 A | 9/1952 | Edwards |
| 2,638,093 A | 5/1953 | Kulick |
| 2,649,619 A | 8/1953 | Killian |
| 2,649,854 A | 8/1953 | Salm |
| 2,690,595 A | 10/1954 | Raiche |
| 2,712,161 A | 7/1955 | Moss |
| 2,856,932 A | 10/1958 | Griffitts |
| 2,912,981 A | 11/1959 | Keough |
| 3,044,468 A | 7/1962 | Birtwell |
| 3,053,257 A | 9/1962 | Birtwell |
| 3,076,464 A | 2/1963 | Rosenberg |
| 3,154,080 A | 10/1964 | Rowan et al. |
| 3,169,527 A | 2/1965 | Sheridan |
| 3,211,151 A | 10/1965 | Foderick et al. |
| 3,304,353 A | 2/1967 | Harautuneian |
| 3,345,988 A | 10/1967 | Vitello |
| 3,394,704 A | 7/1968 | Dery |
| 3,394,705 A | 7/1968 | Abramson |
| 3,403,682 A | 10/1968 | McDonell |
| 3,409,016 A | 11/1968 | Foley |
| 3,434,869 A | 3/1969 | Davidson |
| 3,463,141 A | 8/1969 | Mozolf |
| 3,503,400 A | 3/1970 | Osthagen |
| 3,508,959 A | 4/1970 | Krahnke |
| 3,509,884 A | 5/1970 | Bell |
| 3,520,305 A | 7/1970 | Davis |
| 3,539,674 A | 11/1970 | Dereniuk et al. |
| 3,544,668 A | 12/1970 | Dereniuk |
| 3,548,805 A | 12/1970 | Datsenko |
| 3,556,294 A | 1/1971 | Walck et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,646,929 A | 3/1972 | Bonnar |
| 3,648,704 A | 3/1972 | Jackson |
| 3,683,928 A | 8/1972 | Kuntz |
| 3,695,921 A | 10/1972 | Shepherd et al. |
| 3,699,956 A | 10/1972 | Kitrilakis et al. |
| 3,699,964 A | 10/1972 | Ericson |
| 3,708,324 A | 1/1973 | Stebleton |
| 3,726,281 A | 4/1973 | Norton et al. |
| 3,739,783 A | 6/1973 | Broerman |
| 3,762,399 A | 10/1973 | Riedell |
| 3,768,102 A | 10/1973 | Kwan-Gett et al. |
| 3,788,324 A | 1/1974 | Lim |
| 3,794,042 A | 2/1974 | De Klotz et al. |
| 3,797,478 A | 3/1974 | Walsh et al. |
| 3,838,728 A | 10/1974 | Voegele |
| 3,841,304 A | 10/1974 | Jones |
| 3,854,483 A | 12/1974 | Powers |
| 3,861,395 A | 1/1975 | Taniguchi |
| 3,875,937 A | 4/1975 | Schmitt et al. |
| 3,879,516 A | 4/1975 | Wolvek |
| 3,882,220 A | 5/1975 | Ryder |
| 3,889,685 A | 6/1975 | Miller, Jr. et al. |
| 3,894,540 A | 7/1975 | Bonner, Jr. |
| 3,898,993 A | 8/1975 | Taniguchi |
| 3,903,893 A | 9/1975 | Scheer |
| 3,924,634 A | 12/1975 | Taylor et al. |
| 3,926,705 A | 12/1975 | Todd |
| 3,930,580 A | 1/1976 | Bazell et al. |
| 3,934,721 A | 1/1976 | Juster et al. |
| 3,962,519 A | 6/1976 | Rusch et al. |
| 3,967,728 A | 7/1976 | Gordon et al. |
| 3,981,299 A | 9/1976 | Murray |
| 3,983,879 A | 10/1976 | Todd |
| 4,026,296 A | 5/1977 | Stoy et al. |
| 4,029,104 A | 6/1977 | Kerber |
| 4,055,682 A | 10/1977 | Merrill |
| 4,062,363 A | 12/1977 | Bonner, Jr. |
| 4,091,922 A | 5/1978 | Egler |
| 4,119,094 A | 10/1978 | Micklus et al. |
| 4,120,715 A | 10/1978 | Ockwell et al. |
| 4,133,303 A | 1/1979 | Patel |
| 4,140,127 A | 2/1979 | Cianci et al. |
| 4,149,539 A | 4/1979 | Cianci |
| 4,168,699 A | 9/1979 | Hauser |
| 4,186,745 A | 2/1980 | Lewis et al. |
| 4,187,851 A | 2/1980 | Hauser |
| 4,196,731 A | 4/1980 | Laurin et al. |
| 4,198,983 A | 4/1980 | Becker et al. |
| 4,198,984 A | 4/1980 | Taylor |
| 4,209,010 A | 6/1980 | Ward et al. |
| 4,225,371 A | 9/1980 | Taylor et al. |
| 4,230,115 A | 10/1980 | Walz, Jr. et al. |
| 4,246,909 A | 1/1981 | Wu et al. |
| 4,249,535 A | 2/1981 | Hargest, III |
| 4,252,760 A | 2/1981 | Foster et al. |
| 4,265,848 A | 5/1981 | Rusch |
| 4,266,999 A | 5/1981 | Baier |
| 4,269,310 A | 5/1981 | Uson |
| 4,284,459 A | 8/1981 | Patel et al. |
| 4,287,227 A | 9/1981 | Kamada et al. |
| 4,311,146 A | 1/1982 | Wonder |
| 4,311,659 A | 1/1982 | Rey et al. |
| 4,318,406 A | 3/1982 | McLeod |
| 4,318,947 A | 3/1982 | Joung |
| 4,341,817 A | 7/1982 | Tozier et al. |
| 4,342,392 A | 8/1982 | Cox |
| 4,343,788 A | 8/1982 | Mustacich et al. |
| 4,366,901 A | 1/1983 | Short |
| 4,367,732 A | 1/1983 | Poulsen et al. |
| 4,378,018 A | 3/1983 | Alexander et al. |
| 4,378,796 A | 4/1983 | Milhaud |
| 4,379,506 A | 4/1983 | Davidson |
| 4,381,008 A | 4/1983 | Thomas et al. |
| 4,381,380 A | 4/1983 | LeVeen et al. |
| 4,395,806 A | 8/1983 | Wonder et al. |
| 4,411,648 A | 10/1983 | Davis et al. |
| 4,419,097 A | 12/1983 | Rowland |
| 4,428,365 A | 1/1984 | Hakky |
| 4,446,860 A | 5/1984 | Gutnick |
| 4,457,299 A | 7/1984 | Cornwell |
| 4,472,226 A | 9/1984 | Redinger et al. |
| 4,475,910 A | 10/1984 | Conway et al. |
| 4,477,325 A | 10/1984 | Osburn |
| 4,479,795 A | 10/1984 | Mustacich et al. |
| 4,515,593 A | 5/1985 | Norton |
| 4,534,768 A | 8/1985 | Osburn et al. |
| 4,539,234 A | 9/1985 | Sakamoto et al. |
| 4,540,409 A | 9/1985 | Nystrom et al. |
| 4,553,533 A | 11/1985 | Leighton |
| 4,563,184 A | 1/1986 | Korol |
| 4,568,340 A | 2/1986 | Giacalone |
| 4,571,239 A | 2/1986 | Heyman |
| 4,571,240 A | 2/1986 | Samson et al. |
| 4,576,599 A | 3/1986 | Lipner |
| 4,581,026 A | 4/1986 | Schneider |
| 4,581,028 A | 4/1986 | Fox, Jr. et al. |
| 4,582,762 A | 4/1986 | Onohara et al. |
| 4,586,974 A | 5/1986 | Nystrom et al. |
| 4,589,874 A | 5/1986 | Riedel et al. |
| 4,592,920 A | 6/1986 | Murtfeldt |

(56) References Cited

U.S. PATENT DOCUMENTS

| | | |
|---|---|---|
| 4,597,765 A | 7/1986 | Klatt |
| 4,597,931 A | 7/1986 | Watanabe et al. |
| 4,601,713 A | 7/1986 | Fuqua |
| 4,603,152 A | 7/1986 | Laurin et al. |
| 4,612,337 A | 9/1986 | Fox, Jr. et al. |
| 4,613,324 A | 9/1986 | Ghajar |
| 4,615,692 A | 10/1986 | Giacalone et al. |
| 4,615,697 A | 10/1986 | Robinson |
| 4,622,033 A | 11/1986 | Taniguchi |
| 4,623,329 A | 11/1986 | Drobish et al. |
| 4,626,250 A | 12/1986 | Schneider |
| 4,627,844 A | 12/1986 | Schmitt |
| 4,633,863 A | 1/1987 | Filips et al. |
| 4,634,433 A | 1/1987 | Osborne |
| 4,637,907 A | 1/1987 | Hegel et al. |
| 4,638,790 A | 1/1987 | Conway et al. |
| 4,640,668 A | 2/1987 | Yang |
| 4,640,688 A | 2/1987 | Hauser |
| 4,652,259 A | 3/1987 | O'Neil |
| 4,664,657 A | 5/1987 | Williamitis et al. |
| 4,673,401 A | 6/1987 | Jensen et al. |
| 4,677,143 A | 6/1987 | Laurin et al. |
| 4,685,913 A | 8/1987 | Austin |
| 4,686,124 A | 8/1987 | Onohara et al. |
| 4,687,470 A | 8/1987 | Okada |
| 4,692,152 A | 9/1987 | Emde |
| 4,699,616 A | 10/1987 | Nowak et al. |
| 4,710,169 A | 12/1987 | Christopher |
| 4,710,181 A | 12/1987 | Fuqua |
| 4,713,067 A * | 12/1987 | Rothenberg ............ A61F 5/453 24/30.5 R |
| 4,731,064 A | 3/1988 | Heyden |
| 4,737,219 A | 4/1988 | Taller et al. |
| 4,739,768 A | 4/1988 | Engelson |
| 4,747,845 A | 5/1988 | Korol |
| 4,754,877 A | 7/1988 | Johansson et al. |
| 4,759,753 A | 7/1988 | Schneider et al. |
| 4,768,503 A | 9/1988 | Highgate et al. |
| 4,769,013 A | 9/1988 | Lorenz et al. |
| 4,769,099 A | 9/1988 | Therriault et al. |
| 4,772,473 A | 9/1988 | Patel et al. |
| 4,773,901 A | 9/1988 | Norton |
| 4,775,371 A | 10/1988 | Mueller, Jr. |
| 4,790,834 A | 12/1988 | Austin |
| 4,790,835 A | 12/1988 | Elias |
| D299,865 S | 2/1989 | Kamstrup-Larsen et al. |
| 4,810,247 A | 3/1989 | Glassman |
| 4,811,847 A | 3/1989 | Reif et al. |
| 4,813,935 A | 3/1989 | Haber et al. |
| 4,820,270 A | 4/1989 | Hardcastle et al. |
| 4,820,289 A | 4/1989 | Coury et al. |
| 4,820,291 A | 4/1989 | Terauchi et al. |
| 4,820,292 A | 4/1989 | Korol et al. |
| 4,834,721 A | 5/1989 | Onohara et al. |
| 4,838,876 A | 6/1989 | Wong et al. |
| 4,846,784 A | 7/1989 | Haber |
| 4,846,909 A | 7/1989 | Klug et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,863,449 A | 9/1989 | Therriault et al. |
| 4,867,748 A | 9/1989 | Samuelsen |
| 4,874,373 A | 10/1989 | Luther et al. |
| 4,876,109 A | 10/1989 | Mayer et al. |
| 4,885,049 A | 12/1989 | Johannesson |
| 4,894,059 A | 1/1990 | Larsen et al. |
| 4,902,503 A | 2/1990 | Umemura et al. |
| 4,904,260 A | 2/1990 | Ray et al. |
| 4,917,113 A | 4/1990 | Conway et al. |
| 4,917,686 A | 4/1990 | Bayston et al. |
| 4,919,966 A | 4/1990 | Shlenker |
| RE33,206 E | 5/1990 | Conway et al. |
| 4,923,450 A | 5/1990 | Maeda et al. |
| 4,925,668 A | 5/1990 | Khan et al. |
| 4,930,522 A | 6/1990 | Busnel et al. |
| 4,931,056 A | 6/1990 | Ghajar et al. |
| 4,932,938 A | 6/1990 | Goldberg et al. |
| 4,932,948 A | 6/1990 | Kernes et al. |
| 4,934,999 A | 6/1990 | Bader |
| 4,935,260 A | 6/1990 | Shlenker |
| 4,950,256 A | 8/1990 | Luther et al. |
| 4,952,618 A | 8/1990 | Olsen |
| 4,963,137 A | 10/1990 | Heyden |
| 4,968,294 A | 11/1990 | Salama |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,004,454 A | 4/1991 | Beyar et al. |
| 5,007,897 A | 4/1991 | Kalb et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,059,190 A | 10/1991 | Novak |
| 5,071,406 A | 12/1991 | Jang |
| 5,078,707 A | 1/1992 | Klug |
| 5,082,006 A | 1/1992 | Jonasson |
| 5,084,037 A | 1/1992 | Barnett |
| 5,087,252 A | 2/1992 | Denard |
| 5,088,980 A | 2/1992 | Leighton |
| 5,089,205 A | 2/1992 | Huang et al. |
| 5,090,424 A | 2/1992 | Simon et al. |
| 5,098,379 A | 3/1992 | Conway et al. |
| 5,102,401 A | 4/1992 | Lambert et al. |
| 5,102,405 A | 4/1992 | Conway et al. |
| 5,109,378 A | 4/1992 | Proctor et al. |
| 5,109,601 A | 5/1992 | McBride |
| 5,112,306 A | 5/1992 | Burton et al. |
| 5,114,398 A | 5/1992 | Trick et al. |
| 5,128,088 A | 7/1992 | Shimomura et al. |
| 5,131,906 A | 7/1992 | Chen |
| 5,137,671 A | 8/1992 | Conway et al. |
| 5,140,999 A | 8/1992 | Ardito |
| 5,147,341 A | 9/1992 | Starke et al. |
| 5,165,952 A | 11/1992 | Solomon et al. |
| 5,176,666 A | 1/1993 | Conway et al. |
| 5,197,957 A | 3/1993 | Wendler |
| 5,201,713 A | 4/1993 | Rossetti |
| 5,201,724 A | 4/1993 | Hukins et al. |
| 5,209,726 A | 5/1993 | Goosen |
| 5,211,640 A | 5/1993 | Wendler |
| 5,226,530 A | 7/1993 | Golden |
| 5,234,411 A | 8/1993 | Vaillancourt et al. |
| 5,236,422 A | 8/1993 | Eplett, Jr. |
| 5,242,391 A | 9/1993 | Place et al. |
| 5,242,428 A | 9/1993 | Palestrant |
| 5,261,896 A | 11/1993 | Conway et al. |
| 5,263,947 A | 11/1993 | Kay |
| 5,269,755 A | 12/1993 | Bodicky |
| 5,269,770 A | 12/1993 | Conway et al. |
| 5,270,358 A | 12/1993 | Asmus |
| 5,279,600 A | 1/1994 | Hogan |
| 5,290,306 A | 3/1994 | Trotta et al. |
| 5,300,052 A | 4/1994 | Kubo |
| 5,306,226 A | 4/1994 | Salama |
| 5,312,383 A | 5/1994 | Kubalak |
| 5,334,175 A | 8/1994 | Conway et al. |
| 5,335,775 A | 8/1994 | Scanlon et al. |
| 5,336,211 A | 8/1994 | Metz |
| 5,346,483 A | 9/1994 | Thaxton, Sr. |
| 5,348,536 A | 9/1994 | Young et al. |
| 5,352,182 A | 10/1994 | Kalb et al. |
| 5,360,402 A | 11/1994 | Conway et al. |
| 5,366,449 A | 11/1994 | Gilberg |
| 5,368,575 A | 11/1994 | Chang |
| 5,370,899 A | 12/1994 | Conway et al. |
| 5,376,085 A | 12/1994 | Conway et al. |
| 5,380,312 A | 1/1995 | Goulter |
| 5,395,333 A | 3/1995 | Brill |
| 5,402,886 A | 4/1995 | McGlinch |
| 5,409,495 A | 4/1995 | Osborn |

(56) References Cited

U.S. PATENT DOCUMENTS

| | | |
|---|---|---|
| 5,415,635 A | 5/1995 | Bagaoisan et al. |
| 5,417,226 A | 5/1995 | Juma |
| 5,417,666 A | 5/1995 | Coulter |
| 5,423,784 A | 6/1995 | Metz |
| 5,433,705 A | 7/1995 | Giebel et al. |
| 5,433,713 A | 7/1995 | Trotta |
| 5,447,231 A | 9/1995 | Kastenhofer |
| 5,451,424 A | 9/1995 | Solomon et al. |
| 5,454,798 A | 10/1995 | Kubalak et al. |
| 5,464,650 A | 11/1995 | Berg et al. |
| 5,479,945 A | 1/1996 | Simon |
| 5,482,740 A | 1/1996 | Conway et al. |
| 5,483,976 A | 1/1996 | McLaughlin et al. |
| 5,501,669 A | 3/1996 | Conway et al. |
| 5,509,427 A | 4/1996 | Simon et al. |
| 5,513,659 A | 5/1996 | Buuck et al. |
| 5,513,660 A | 5/1996 | Simon et al. |
| 5,531,715 A | 7/1996 | Engelson et al. |
| 5,531,717 A | 7/1996 | Roberto et al. |
| 5,538,584 A | 7/1996 | Metz |
| 5,549,924 A | 8/1996 | Shlenker et al. |
| 5,554,141 A | 9/1996 | Wendler |
| 5,562,599 A | 10/1996 | Beyschlag |
| 5,567,495 A | 10/1996 | Modak et al. |
| 5,569,219 A | 10/1996 | Hakki et al. |
| 5,582,599 A | 12/1996 | Daneshvar |
| 5,593,718 A | 1/1997 | Conway et al. |
| 5,599,321 A | 2/1997 | Conway et al. |
| 5,614,143 A | 3/1997 | Hager |
| 5,622,711 A | 4/1997 | Chen |
| 5,624,395 A | 4/1997 | Mikhail et al. |
| 5,630,429 A | 5/1997 | Dann |
| 5,633,010 A | 5/1997 | Chen |
| 5,634,475 A | 6/1997 | Wolvek |
| 5,643,235 A | 7/1997 | Figuerido |
| 5,670,111 A | 9/1997 | Conway et al. |
| 5,670,557 A | 9/1997 | Dietz et al. |
| 5,671,755 A | 9/1997 | Simon et al. |
| 5,674,561 A | 10/1997 | Dietz et al. |
| 5,679,399 A | 10/1997 | Shlenker et al. |
| 5,695,485 A | 12/1997 | Duperret et al. |
| 5,702,381 A | 12/1997 | Cottenden |
| 5,707,357 A | 1/1998 | Mikhail et al. |
| 5,709,672 A | 1/1998 | Illner |
| 5,711,841 A | 1/1998 | Jaker |
| 5,724,994 A | 3/1998 | Simon et al. |
| 5,730,733 A | 3/1998 | Mortier et al. |
| 5,736,152 A | 4/1998 | Dunn |
| 5,752,525 A | 5/1998 | Simon et al. |
| 5,752,944 A | 5/1998 | Dann et al. |
| 5,756,144 A | 5/1998 | Wolff et al. |
| 5,762,996 A | 6/1998 | Lucas et al. |
| 5,779,632 A | 7/1998 | Dietz et al. |
| 5,779,670 A | 7/1998 | Bidwell et al. |
| 5,795,332 A | 8/1998 | Lucas et al. |
| 5,795,334 A | 8/1998 | Cochrane, III |
| 5,795,524 A | 8/1998 | Basso, Jr. et al. |
| 5,806,527 A | 9/1998 | Borodulin et al. |
| 5,810,789 A | 9/1998 | Powers et al. |
| 5,820,607 A | 10/1998 | Tcholakian et al. |
| 5,827,247 A | 10/1998 | Kay |
| 5,827,249 A | 10/1998 | Jensen |
| 5,830,932 A | 11/1998 | Kay |
| 5,853,518 A | 12/1998 | Utas |
| 5,853,750 A | 12/1998 | Dietz et al. |
| 5,865,821 A | 2/1999 | Lowey |
| 5,877,243 A | 3/1999 | Sarangapani |
| 5,895,374 A | 4/1999 | Rødsten |
| 5,897,535 A | 4/1999 | Feliziani et al. |
| 5,902,631 A | 5/1999 | Wang et al. |
| 5,906,575 A | 5/1999 | Conway et al. |
| 5,931,303 A | 8/1999 | Salvadori |
| 5,931,304 A | 8/1999 | Hammond |
| 5,971,954 A | 10/1999 | Conway et al. |
| 5,980,483 A | 11/1999 | Dimitri |
| 5,980,507 A | 11/1999 | Fassuliotis et al. |
| 6,004,305 A | 12/1999 | Hursman et al. |
| 6,007,524 A | 12/1999 | Schneider |
| 6,007,526 A | 12/1999 | Passalaqua et al. |
| 6,042,562 A | 3/2000 | Amor |
| 6,050,934 A | 4/2000 | Mikhail et al. |
| 6,053,905 A | 4/2000 | Daignault, Jr. et al. |
| 6,059,107 A | 5/2000 | Nøsted et al. |
| 6,063,063 A | 5/2000 | Harboe et al. |
| 6,065,597 A | 5/2000 | Pettersson et al. |
| 6,068,618 A | 5/2000 | Anderson |
| 6,090,075 A | 7/2000 | House |
| 6,098,625 A | 8/2000 | Winkler |
| 6,102,929 A | 8/2000 | Conway et al. |
| 6,113,582 A | 9/2000 | Dwork |
| 6,119,697 A | 9/2000 | Engel et al. |
| 6,131,575 A | 10/2000 | Lenker et al. |
| 6,132,399 A | 10/2000 | Shultz |
| 6,186,990 B1 | 2/2001 | Chen et al. |
| 6,206,885 B1 | 3/2001 | Ghahremani et al. |
| 6,231,501 B1 | 5/2001 | Ditter |
| 6,254,570 B1 | 7/2001 | Rutner et al. |
| 6,261,255 B1 | 7/2001 | Mullis et al. |
| 6,261,271 B1 | 7/2001 | Solomon et al. |
| 6,280,425 B1 | 8/2001 | Del Guercio |
| 6,296,627 B1 | 10/2001 | Edwards |
| 6,299,598 B1 | 10/2001 | Bander |
| 6,315,711 B1 | 11/2001 | Conway et al. |
| 6,326,421 B1 | 12/2001 | Lipman |
| 6,355,004 B1 | 3/2002 | Pedersen et al. |
| 6,379,334 B1 | 4/2002 | Frassica |
| 6,383,434 B2 | 5/2002 | Conway et al. |
| 6,387,080 B1 | 5/2002 | Rødsten |
| 6,391,010 B1 | 5/2002 | Wilcox |
| 6,402,726 B1 | 6/2002 | Genese |
| 6,409,717 B1 | 6/2002 | Israelsson et al. |
| 6,436,085 B1 | 8/2002 | Lauer |
| 6,437,038 B1 | 8/2002 | Chen |
| 6,440,060 B1 | 8/2002 | Latour, Jr. |
| 6,468,245 B2 | 10/2002 | Alexandersen |
| 6,471,268 B1 | 10/2002 | Stenstrom et al. |
| 6,479,000 B2 | 11/2002 | Conway et al. |
| 6,479,726 B1 | 11/2002 | Cole |
| 6,509,319 B1 | 1/2003 | Raad et al. |
| 6,551,293 B1 | 4/2003 | Mitchell |
| 6,558,369 B2 | 5/2003 | Rosenblum |
| 6,558,792 B1 | 5/2003 | Vaabengaard et al. |
| 6,578,709 B1 | 6/2003 | Kavanagh et al. |
| 6,579,539 B2 | 6/2003 | Lawson et al. |
| 6,582,401 B1 | 6/2003 | Windheuser et al. |
| 6,596,401 B1 | 7/2003 | Terry et al. |
| 6,602,244 B2 | 8/2003 | Kavanagh et al. |
| 6,613,014 B1 | 9/2003 | Chi |
| 6,626,888 B1 | 9/2003 | Conway et al. |
| 6,632,204 B2 | 10/2003 | Guldfeldt et al. |
| 6,634,498 B2 | 10/2003 | Kayerød et al. |
| 6,638,269 B2 | 10/2003 | Wilcox |
| 6,659,937 B2 | 12/2003 | Polsky et al. |
| 6,682,555 B2 | 1/2004 | Cioanta et al. |
| 6,693,189 B2 | 2/2004 | Holt et al. |
| 6,695,831 B1 | 2/2004 | Tsukada et al. |
| 6,716,895 B1 | 4/2004 | Terry |
| 6,719,709 B2 | 4/2004 | Whalen et al. |
| 6,723,350 B2 | 4/2004 | Burrell et al. |
| 6,733,474 B2 | 5/2004 | Kusleika |
| 6,736,805 B2 | 5/2004 | Israelsson et al. |
| 6,740,273 B2 | 5/2004 | Lee |
| 6,767,551 B2 | 7/2004 | McGhee et al. |
| D496,266 S | 9/2004 | Nestenborg |
| 6,787,156 B1 | 9/2004 | Bar-Shalom |
| 6,797,743 B2 | 9/2004 | McDonald et al. |
| 6,803,420 B2 | 10/2004 | Cleary et al. |
| 6,848,574 B1 | 2/2005 | Israelsson et al. |
| 6,849,070 B1 | 2/2005 | Hansen et al. |
| 6,852,105 B2 | 2/2005 | Bolmsjo et al. |
| D503,335 S | 3/2005 | Risberg et al. |
| 6,869,416 B2 | 3/2005 | Windheuser et al. |
| 6,872,195 B2 | 3/2005 | Modak et al. |
| 6,887,230 B2 | 5/2005 | Kubalak et al. |

(56) References Cited

U.S. PATENT DOCUMENTS

| | | |
|---|---|---|
| 6,939,339 B1 | 9/2005 | Axexandersen et al. |
| 6,939,554 B2 | 9/2005 | McDonald et al. |
| 6,949,090 B1 | 9/2005 | Leers et al. |
| 6,951,902 B2 | 10/2005 | McDonald et al. |
| 7,001,370 B2 | 2/2006 | Kubalak et al. |
| 7,033,367 B2 | 4/2006 | Ghahremani et al. |
| 7,066,912 B2 | 6/2006 | Nestenborg et al. |
| 7,087,048 B2 | 8/2006 | Israelsson et al. |
| 7,094,220 B2 | 8/2006 | Tanghoj et al. |
| 7,160,277 B2 | 1/2007 | Elson et al. |
| 7,166,092 B2 | 1/2007 | Elson et al. |
| 7,204,940 B2 | 4/2007 | McDonald et al. |
| 7,211,275 B2 | 5/2007 | Ying et al. |
| 7,294,117 B2 | 11/2007 | Provost-tine et al. |
| 7,311,698 B2 | 12/2007 | Tanghoj et al. |
| 7,329,412 B2 | 2/2008 | Modak et al. |
| 7,331,948 B2 | 2/2008 | Skarda |
| 7,334,679 B2 | 2/2008 | Givens, Jr. |
| 7,374,040 B2 | 5/2008 | Lee et al. |
| 7,380,658 B2 | 6/2008 | Murray et al. |
| 7,381,768 B2 | 6/2008 | Wiercinski et al. |
| 7,402,559 B2 | 7/2008 | Catania et al. |
| 7,445,812 B2 | 11/2008 | Schmidt et al. |
| 7,458,964 B2 | 12/2008 | Mosler et al. |
| 7,476,223 B2 | 1/2009 | McBride |
| 7,507,229 B2 | 3/2009 | Hewitt et al. |
| 7,517,343 B2 | 4/2009 | Tanghoj et al. |
| 7,571,804 B2 | 8/2009 | Kjellmann Bruun et al. |
| 7,601,158 B2 | 10/2009 | House |
| 7,615,045 B2 | 11/2009 | Israelsson et al. |
| 7,628,784 B2 | 12/2009 | Diaz et al. |
| 7,632,256 B2 | 12/2009 | Mosler et al. |
| D609,819 S | 2/2010 | Tomes et al. |
| 7,662,146 B2 | 2/2010 | House |
| 7,670,331 B2 | 3/2010 | Tanghoej |
| 7,682,353 B2 | 3/2010 | Tanghoj et al. |
| 7,691,476 B2 | 4/2010 | Finley |
| 7,717,902 B2 | 5/2010 | Sauer |
| 7,749,529 B2 | 7/2010 | Ash et al. |
| 7,767,291 B2 | 8/2010 | Faylor |
| 7,770,726 B2 | 8/2010 | Murray et al. |
| 7,770,728 B2 | 8/2010 | Kærn |
| 7,780,642 B2 | 8/2010 | Rasmussen et al. |
| 7,789,873 B2 | 9/2010 | Kubalak et al. |
| 7,823,722 B2 | 11/2010 | Bezou et al. |
| 7,846,133 B2 | 12/2010 | Windheuser et al. |
| 7,867,220 B2 | 1/2011 | Tanghoj |
| 7,886,907 B2 | 2/2011 | Murray et al. |
| 7,918,831 B2 | 4/2011 | House |
| 7,938,838 B2 | 5/2011 | House |
| 7,947,021 B2 | 5/2011 | Bourne et al. |
| 7,985,217 B2 | 7/2011 | Mosler et al. |
| 8,011,505 B2 | 9/2011 | Murray et al. |
| 8,051,981 B2 | 11/2011 | Murray et al. |
| 8,052,673 B2 | 11/2011 | Nestenborg |
| 8,058,341 B2 | 11/2011 | Tosaki et al. |
| 8,066,693 B2 | 11/2011 | Tanghoj et al. |
| 8,127,922 B2 | 3/2012 | Nordholm et al. |
| 8,163,327 B2 | 4/2012 | Finley |
| 8,177,774 B2 | 5/2012 | House |
| 8,181,778 B1 | 5/2012 | van Groningen et al. |
| 8,192,413 B2 | 6/2012 | Bjerregaard |
| 8,205,745 B2 | 6/2012 | Murray et al. |
| 8,207,393 B2 | 6/2012 | Bach |
| 8,230,993 B2 | 7/2012 | Tanghoej |
| 8,267,919 B2 | 9/2012 | Utas et al. |
| 8,282,624 B2 | 10/2012 | Tanghoej et al. |
| 8,287,519 B2 | 10/2012 | Smith |
| 8,298,202 B2 | 10/2012 | McCray |
| 8,303,556 B2 | 11/2012 | White |
| 8,328,792 B2 | 12/2012 | Nishtala et al. |
| 8,356,457 B2 | 1/2013 | Murray et al. |
| 8,409,171 B2 | 4/2013 | Hannon et al. |
| 8,454,569 B2 | 6/2013 | Kull-Osterlin et al. |
| 8,459,455 B2 | 6/2013 | Frojd |
| 8,475,434 B2 | 7/2013 | Frojd |
| 8,864,730 B2 | 10/2014 | Conway et al. |
| 9,707,375 B2 | 7/2017 | Conway et al. |
| 9,872,969 B2 | 1/2018 | Conway et al. |
| 10,092,728 B2 | 10/2018 | Conway et al. |
| 10,569,051 B2 | 2/2020 | Conway et al. |
| 10,639,451 B2 | 5/2020 | Kearns et al. |
| 10,702,671 B2 | 7/2020 | Terry |
| 2001/0001443 A1 | 5/2001 | Kayerod et al. |
| 2001/0031933 A1 | 10/2001 | Cannon |
| 2001/0054562 A1 | 12/2001 | Pettersson et al. |
| 2002/0013564 A1 | 1/2002 | Kubalek et al. |
| 2002/0032406 A1 | 3/2002 | Kusleika |
| 2002/0103467 A1 | 8/2002 | Kubalak |
| 2002/0147265 A1 | 10/2002 | Ding et al. |
| 2002/0169438 A1 | 11/2002 | Sauer |
| 2002/0182265 A1 | 12/2002 | Burrell et al. |
| 2003/0004496 A1 | 1/2003 | Tanghoj |
| 2003/0018293 A1 | 1/2003 | Tanghoj et al. |
| 2003/0018302 A1 | 1/2003 | Kavanagh et al. |
| 2003/0018321 A1 | 1/2003 | Rosenblum |
| 2003/0018322 A1 | 1/2003 | Tanghoj et al. |
| 2003/0055403 A1 | 3/2003 | Nestenborg et al. |
| 2003/0060807 A1 | 3/2003 | Tanghoj et al. |
| 2003/0083644 A1 | 5/2003 | Avaltroni |
| 2003/0114823 A1 | 6/2003 | Bosselaar et al. |
| 2003/0130646 A1 | 7/2003 | Kubalak et al. |
| 2003/0168365 A1 | 9/2003 | Kaern |
| 2004/0030301 A1 | 2/2004 | Hunter |
| 2004/0055925 A1 | 3/2004 | Franks-Farah et al. |
| 2004/0074794 A1 | 4/2004 | Conway et al. |
| 2004/0082926 A1 | 4/2004 | Bruns |
| 2004/0097892 A1 | 5/2004 | Evans et al. |
| 2004/0133156 A1 | 7/2004 | Diaz et al. |
| 2004/0133226 A1 | 7/2004 | Buckman et al. |
| 2004/0153049 A1 | 8/2004 | Hewitt et al. |
| 2004/0153051 A1 | 8/2004 | Israelsson et al. |
| 2004/0158231 A1 | 8/2004 | Tanghoj et al. |
| 2004/0163980 A1 | 8/2004 | Tanghoj et al. |
| 2004/0193143 A1 | 9/2004 | Sauer |
| 2004/0234572 A1 | 11/2004 | Martinod et al. |
| 2004/0236293 A1 | 11/2004 | Tanghoj et al. |
| 2004/0249343 A1 | 12/2004 | Cioanta |
| 2004/0254562 A1 | 12/2004 | Tanghoj et al. |
| 2004/0256264 A1 | 12/2004 | Israelsson et al. |
| 2005/0015076 A1 | 1/2005 | Giebmeyer et al. |
| 2005/0031872 A1 | 2/2005 | Schmidt et al. |
| 2005/0043715 A1 | 2/2005 | Nestenborg et al. |
| 2005/0049577 A1 | 3/2005 | Snell et al. |
| 2005/0070882 A1 | 3/2005 | McBride |
| 2005/0080399 A1 | 4/2005 | Bolmsjo et al. |
| 2005/0096688 A1 | 5/2005 | Slazas et al. |
| 2005/0101924 A1 | 5/2005 | Elson et al. |
| 2005/0109648 A1 | 5/2005 | Kerzman et al. |
| 2005/0137582 A1 | 6/2005 | Kull-Osterlin et al. |
| 2005/0148950 A1 | 7/2005 | Windheuser et al. |
| 2005/0177104 A1 | 8/2005 | Conway |
| 2005/0199521 A1 | 9/2005 | Givens |
| 2005/0214443 A1 | 9/2005 | Madsen |
| 2005/0282977 A1 | 12/2005 | Stempel et al. |
| 2005/0283136 A1 | 12/2005 | Skarda |
| 2006/0004332 A1 | 1/2006 | Marx |
| 2006/0025753 A1 | 2/2006 | Kubalak et al. |
| 2006/0041246 A1 | 2/2006 | Provost-tine et al. |
| 2006/0058777 A1 | 3/2006 | Nielsen |
| 2006/0196783 A1 | 9/2006 | Bruun et al. |
| 2006/0229576 A1 | 10/2006 | Conway et al. |
| 2006/0240069 A1 | 10/2006 | Utas et al. |
| 2007/0016168 A1 | 1/2007 | Conway |
| 2007/0026472 A1 | 2/2007 | Prokash et al. |
| 2007/0088330 A1 | 4/2007 | House |
| 2007/0149946 A1 | 6/2007 | Viswanathan et al. |
| 2007/0161971 A1 | 7/2007 | House |
| 2008/0015527 A1 | 1/2008 | House |
| 2008/0082051 A1 | 4/2008 | Miller et al. |
| 2008/0091145 A1 | 4/2008 | House |
| 2008/0103464 A1 | 5/2008 | Mosler et al. |
| 2008/0119803 A1 | 5/2008 | Lund |
| 2008/0172040 A1 | 7/2008 | Smith |

(56) References Cited

U.S. PATENT DOCUMENTS

| | | | |
|---|---|---|---|
| 2008/0172042 A1 | 7/2008 | House | |
| 2008/0179208 A1 | 7/2008 | Murray et al. | |
| 2008/0183262 A1 | 7/2008 | Dowling | |
| 2008/0215021 A1 | 9/2008 | Cisko, Jr. et al. | |
| 2008/0243081 A1 | 10/2008 | Nance et al. | |
| 2008/0279907 A1 | 11/2008 | Ash et al. | |
| 2009/0000970 A1 | 1/2009 | Bordeau et al. | |
| 2009/0005725 A1 | 1/2009 | Shorey | |
| 2009/0043287 A1 | 2/2009 | Mosler et al. | |
| 2009/0048570 A1 | 2/2009 | Jensen | |
| 2009/0101531 A1 | 4/2009 | Nordholm et al. | |
| 2009/0131917 A1 | 5/2009 | Kavanagh et al. | |
| 2009/0163884 A1 | 6/2009 | Kull-Osterlin et al. | |
| 2009/0200187 A1 | 8/2009 | Nestenborg et al. | |
| 2009/0208368 A1 | 8/2009 | Waldrep et al. | |
| 2009/0221992 A1 | 9/2009 | Hannon et al. | |
| 2009/0234294 A1 | 9/2009 | Harvey et al. | |
| 2009/0240214 A1 | 9/2009 | Conway et al. | |
| 2009/0247827 A1 | 10/2009 | Secrest et al. | |
| 2010/0010086 A1 | 1/2010 | Ash et al. | |
| 2010/0025273 A1 | 2/2010 | Matsuda et al. | |
| 2010/0030197 A1 | 2/2010 | House | |
| 2010/0036363 A1 | 2/2010 | Watanabe et al. | |
| 2010/0074669 A1 | 3/2010 | Liu | |
| 2010/0133172 A1 | 6/2010 | Song et al. | |
| 2010/0155268 A1 | 6/2010 | Murray et al. | |
| 2010/0200002 A1 | 8/2010 | Orban, III et al. | |
| 2010/0240750 A1 | 9/2010 | Ash et al. | |
| 2010/0256576 A1 | 10/2010 | Aggarwal et al. | |
| 2010/0322996 A1 | 12/2010 | Wibaux et al. | |
| 2011/0056852 A1 | 3/2011 | Frojd | |
| 2011/0060317 A1 | 3/2011 | Frojd | |
| 2011/0100526 A1 | 5/2011 | Umebayashi | |
| 2011/0114520 A1 | 5/2011 | Matthison-Hansen | |
| 2011/0118670 A1 | 5/2011 | Kay et al. | |
| 2011/0137296 A1 | 6/2011 | Tanghoj | |
| 2011/0152843 A1 | 6/2011 | Wedlin et al. | |
| 2011/0178507 A1 | 7/2011 | Bracken et al. | |
| 2011/0184386 A1 | 7/2011 | House | |
| 2011/0213025 A1 | 9/2011 | Finch, Jr. | |
| 2011/0284409 A1 | 11/2011 | Murray et al. | |
| 2012/0029451 A1 | 2/2012 | Conway | |
| 2012/0145589 A1* | 6/2012 | Macinnes | A61M 25/002 206/571 |
| 2012/0179144 A1 | 7/2012 | Carleo | |
| 2012/0203182 A1 | 8/2012 | Kay et al. | |
| 2012/0228165 A1 | 9/2012 | Murray et al. | |
| 2012/0271101 A1 | 10/2012 | Tan | |
| 2012/0316515 A1 | 12/2012 | Terry | |
| 2013/0006226 A1 | 1/2013 | Hong et al. | |
| 2013/0037306 A1 | 2/2013 | Kim | |
| 2013/0112589 A1 | 5/2013 | Lien et al. | |
| 2013/0131647 A1 | 5/2013 | Nielsen | |
| 2013/0138083 A1 | 5/2013 | Tennican | |
| 2013/0138088 A1 | 5/2013 | Nielsen | |
| 2013/0153446 A1 | 6/2013 | Utas et al. | |
| 2014/0142554 A1 | 5/2014 | Conway et al. | |
| 2014/0142555 A1 | 5/2014 | Conway et al. | |
| 2014/0262252 A1* | 9/2014 | Slepicka | A61M 5/172 166/255.2 |
| 2015/0025489 A1 | 1/2015 | Conway et al. | |
| 2017/0021135 A1 | 1/2017 | Engelhardt | |
| 2017/0216558 A1 | 8/2017 | Hughett et al. | |
| 2017/0304590 A1 | 10/2017 | Conway et al. | |
| 2018/0133434 A1 | 5/2018 | Conway et al. | |
| 2020/0179647 A1 | 6/2020 | Conway et al. | |
| 2020/0398023 A1 | 12/2020 | Conway et al. | |

FOREIGN PATENT DOCUMENTS

| | | |
|---|---|---|
| CN | 201248791 Y | 6/2009 |
| CN | 101896218 A | 11/2010 |
| CN | 202173496 U | 3/2012 |
| DE | 1913976 U | 4/1965 |
| DE | 19826746 C1 | 11/1999 |
| EP | 0055023 A2 | 6/1982 |
| EP | 0182409 A1 | 5/1986 |
| EP | 0184629 A2 | 6/1986 |
| EP | 0187846 A1 | 7/1986 |
| EP | 0193406 A2 | 9/1986 |
| EP | 0218203 A1 | 4/1987 |
| EP | 0236458 A1 | 9/1987 |
| EP | 0252918 A1 | 1/1988 |
| EP | 0298634 A1 | 1/1989 |
| EP | 0303487 A2 | 2/1989 |
| EP | 0335564 A1 | 10/1989 |
| EP | 0352043 A1 | 1/1990 |
| EP | 0390720 A1 | 10/1990 |
| EP | 0407218 A1 | 1/1991 |
| EP | 0217771 B1 | 12/1991 |
| EP | 0471553 A1 | 2/1992 |
| EP | 0479935 A1 | 4/1992 |
| EP | 0528965 A1 | 3/1993 |
| EP | 0553960 A1 | 8/1993 |
| EP | 0590104 A1 | 4/1994 |
| EP | 0598191 A1 | 5/1994 |
| EP | 0663196 A1 | 7/1995 |
| EP | 0677299 A1 | 10/1995 |
| EP | 0680895 A1 | 11/1995 |
| EP | 0685179 A1 | 12/1995 |
| EP | 0699086 A1 | 3/1996 |
| EP | 0767639 A1 | 4/1997 |
| EP | 0768069 A1 | 4/1997 |
| EP | 0815037 A1 | 1/1998 |
| EP | 0909249 A1 | 4/1999 |
| EP | 0923398 A1 | 6/1999 |
| EP | 0935478 A1 | 8/1999 |
| EP | 0972536 A1 | 1/2000 |
| EP | 0977610 A2 | 2/2000 |
| EP | 1023882 A1 | 8/2000 |
| EP | 1047360 A1 | 11/2000 |
| EP | 1115450 A1 | 7/2001 |
| EP | 1131022 A1 | 9/2001 |
| EP | 1245205 A2 | 10/2002 |
| EP | 0959930 B1 | 12/2002 |
| EP | 1308146 A1 | 5/2003 |
| EP | 1347723 A1 | 10/2003 |
| EP | 1406690 A2 | 4/2004 |
| EP | 1090656 B1 | 5/2004 |
| EP | 1427467 A2 | 6/2004 |
| EP | 1485158 A2 | 12/2004 |
| EP | 1498151 A2 | 1/2005 |
| EP | 1578308 A1 | 9/2005 |
| EP | 1145729 B1 | 11/2005 |
| EP | 1606196 A2 | 12/2005 |
| EP | 1615690 A1 | 1/2006 |
| EP | 1629799 A1 | 3/2006 |
| EP | 1641510 A1 | 4/2006 |
| EP | 1642610 | 4/2006 |
| EP | 1642611 | 4/2006 |
| EP | 1647298 A2 | 4/2006 |
| EP | 1786501 A2 | 5/2007 |
| EP | 1788990 A1 | 5/2007 |
| EP | 1793938 A1 | 6/2007 |
| EP | 1799163 A1 | 6/2007 |
| EP | 1904003 A2 | 4/2008 |
| EP | 1948279 A1 | 7/2008 |
| EP | 1955683 A1 | 8/2008 |
| EP | 2072075 A1 | 6/2009 |
| EP | 2216064 A1 | 8/2010 |
| EP | 2226041 A2 | 9/2010 |
| EP | 2226042 A2 | 9/2010 |
| EP | 2258435 A1 | 12/2010 |
| EP | 2275058 A1 | 1/2011 |
| EP | 2292293 A1 | 3/2011 |
| EP | 2292294 A1 | 3/2011 |
| EP | 2423125 A1 | 2/2012 |
| EP | 2423126 A1 | 2/2012 |
| EP | 2423127 A1 | 2/2012 |
| EP | 2450076 A1 | 5/2012 |
| EP | 2468347 A1 | 6/2012 |
| FR | 1558162 A | 2/1969 |
| FR | 2794638 A1 | 12/2000 |

(56) References Cited

FOREIGN PATENT DOCUMENTS

| | | |
|---|---|---|
| FR | 2855399 A1 | 12/2004 |
| GB | 322426 A | 12/1929 |
| GB | 1131865 A | 10/1968 |
| GB | 2150938 A | 7/1985 |
| GB | 2187670 A | 9/1987 |
| JP | 2010-533562 A | 10/2010 |
| JP | 2011-506009 A | 3/2011 |
| WO | 1984001102 A1 | 3/1984 |
| WO | 1986000816 A1 | 2/1986 |
| WO | 1986006284 A1 | 11/1986 |
| WO | 1987001582 A1 | 3/1987 |
| WO | 1989009626 A1 | 10/1989 |
| WO | 1990004431 A1 | 5/1990 |
| WO | 1991010466 A1 | 7/1991 |
| WO | 1991010467 A1 | 7/1991 |
| WO | 1991017728 A1 | 11/1991 |
| WO | 1992008426 A1 | 5/1992 |
| WO | 1992010220 A1 | 6/1992 |
| WO | 1992011826 A1 | 7/1992 |
| WO | 1992019192 A1 | 11/1992 |
| WO | 1993000054 A1 | 1/1993 |
| WO | 1993011821 A1 | 6/1993 |
| WO | 1993014806 A1 | 8/1993 |
| WO | 1994006377 A1 | 3/1994 |
| WO | 1994016747 A1 | 8/1994 |
| WO | 1994026215 A1 | 11/1994 |
| WO | 1995008968 A1 | 4/1995 |
| WO | 1995009667 A1 | 4/1995 |
| WO | 1995017862 A1 | 7/1995 |
| WO | 1995034253 A1 | 12/1995 |
| WO | 1996000541 A1 | 1/1996 |
| WO | 1996004119 A1 | 2/1996 |
| WO | 1996019254 A1 | 6/1996 |
| WO | 1996026688 A1 | 9/1996 |
| WO | 1996030277 A1 | 10/1996 |
| WO | 1996034587 A1 | 11/1996 |
| WO | 1996038192 A1 | 12/1996 |
| WO | 1996039096 A1 | 12/1996 |
| WO | 1997025947 A1 | 7/1997 |
| WO | 1997026937 A1 | 7/1997 |
| WO | 1997041811 A1 | 11/1997 |
| WO | 1998006642 A1 | 2/1998 |
| WO | 1999007313 A1 | 2/1999 |
| WO | 1999030761 A1 | 6/1999 |
| WO | 1999036009 A1 | 7/1999 |
| WO | 2000025848 A2 | 5/2000 |
| WO | 2000030575 A1 | 6/2000 |
| WO | 2000047494 A1 | 8/2000 |
| WO | 2001043807 A1 | 6/2001 |
| WO | 2001052763 A1 | 7/2001 |
| WO | 2001093935 A1 | 12/2001 |
| WO | 2002036192 A1 | 5/2002 |
| WO | 2002053070 A1 | 7/2002 |
| WO | 2002060361 A2 | 8/2002 |
| WO | 03/008028 A2 | 1/2003 |
| WO | 2003002178 A2 | 1/2003 |
| WO | 2003008029 A2 | 1/2003 |
| WO | 2003/022333 A1 | 3/2003 |
| WO | 2003064279 A1 | 8/2003 |
| WO | 2003092779 A1 | 11/2003 |
| WO | 2004004611 A1 | 1/2004 |
| WO | 2004004796 A1 | 1/2004 |
| WO | 2004030722 A2 | 4/2004 |
| WO | 2004032992 A2 | 4/2004 |
| WO | 2004045696 | 6/2004 |
| WO | 2004050155 A1 | 6/2004 |
| WO | 2004052440 A1 | 6/2004 |
| WO | 2004056290 A1 | 7/2004 |
| WO | 2004056414 A1 | 7/2004 |
| WO | 2004056909 A1 | 7/2004 |
| WO | 2004075944 A2 | 9/2004 |
| WO | 2004089454 A1 | 10/2004 |
| WO | 2005004964 A1 | 1/2005 |
| WO | 2005014055 A2 | 2/2005 |
| WO | 2005061035 A1 | 7/2005 |
| WO | 2005092418 A1 | 10/2005 |
| WO | 2006005349 A2 | 1/2006 |
| WO | 2006009509 A1 | 1/2006 |
| WO | 2006009596 A1 | 1/2006 |
| WO | 2006017439 A2 | 2/2006 |
| WO | 2006021590 A1 | 3/2006 |
| WO | 2006027349 A1 | 3/2006 |
| WO | 2006/086250 A2 | 8/2006 |
| WO | 2006097109 A2 | 9/2006 |
| WO | 2006110695 A2 | 10/2006 |
| WO | 2006112782 A1 | 10/2006 |
| WO | 2006130776 A2 | 12/2006 |
| WO | 2007001526 A2 | 1/2007 |
| WO | 2007038988 A1 | 4/2007 |
| WO | 2007083033 A2 | 7/2007 |
| WO | 2008089770 A1 | 7/2008 |
| WO | 2008104603 A1 | 9/2008 |
| WO | 2008138351 A1 | 11/2008 |
| WO | 2008138352 A1 | 11/2008 |
| WO | 2009000277 A1 | 12/2008 |
| WO | 2009012336 A1 | 1/2009 |
| WO | 2009043872 A1 | 4/2009 |
| WO | 2009068043 A2 | 6/2009 |
| WO | 2009080265 A1 | 7/2009 |
| WO | 2009108243 A1 | 9/2009 |
| WO | 2010006620 A1 | 1/2010 |
| WO | 2010054659 A1 | 5/2010 |
| WO | 2010054666 A1 | 5/2010 |
| WO | 2010129362 A1 | 11/2010 |
| WO | 2010130261 A1 | 11/2010 |
| WO | 2010149174 A1 | 12/2010 |
| WO | 2010149175 A1 | 12/2010 |
| WO | 2010151682 A2 | 12/2010 |
| WO | 2011011023 A1 | 1/2011 |
| WO | 2011014201 A1 | 2/2011 |
| WO | 2011019359 A1 | 2/2011 |
| WO | 2011026929 A1 | 3/2011 |
| WO | 2011026930 A1 | 3/2011 |
| WO | 2011063816 A1 | 6/2011 |
| WO | 2011073403 A1 | 6/2011 |
| WO | 2011076211 A1 | 6/2011 |
| WO | 2011079129 A1 | 6/2011 |
| WO | 2011109393 A1 | 9/2011 |
| WO | 2012016570 A2 | 2/2012 |
| WO | 2012016571 A2 | 2/2012 |
| WO | 2012018402 A1 | 2/2012 |
| WO | 2012079590 A1 | 6/2012 |
| WO | 2012134804 A1 | 10/2012 |
| WO | 2013010745 A1 | 1/2013 |
| WO | 2013029621 A1 | 3/2013 |
| WO | 2014081853 A1 | 5/2014 |
| WO | 2014081859 A1 | 5/2014 |

OTHER PUBLICATIONS

U.S. Appl. No. 13/682,420, filed Nov. 20, 2012 Non-Final Office Action dated Apr. 2, 2014.
U.S. Appl. No. 13/705,695, filed Dec. 5, 2012 Final Office Action dated Apr. 23, 2015.
U.S. Appl. No. 13/705,695, filed Dec. 5, 2012 Non-Final Office Action dated Aug. 26, 2014.
U.S. Appl. No. 14/508,450, filed Oct. 7, 2014 Non-Final Office Action dated Jun. 29, 2015.
U.S. Appl. No. 15/649,296, filed Jul. 31, 2017 Non-Final Office Action dated Jul. 30, 2019.
U.S. Appl. No. 15/649,296, filed Jul. 31, 2017 Notice of Allowance dated Oct. 17, 2019.
U.S. Appl. No. 15/869,758, filed Jan. 12, 2018 Non-Final Office Action dated Mar. 23, 2020.
U.S. Appl. No. 15/869,758, filed Jan. 12, 2018 Notice of Allowance dated May 29, 2020.
Vapro Product Brochure, 2009.
PCT/US2018/051550 filed Sep. 18, 2018 International Preliminary report on Patentability dated Mar. 24, 2020.
PCT/US2018/051550 filed Sep. 18, 2018 International Search Report and Written Opinion dated Nov. 30, 2018.

(56) References Cited

OTHER PUBLICATIONS

Amirkhalili, Saeid et al., "Mitric Oxide Complexes of Trimethylaluminium," Jornal of Organometallic Chemistry, 149 (Jan. 20, 1978) 407-411.
Angus Chemie GmbH Technical Data Sheet for AMP-95 dated Mar. 6, 2006.
CN 201380060729.1 filed May 20, 2015 Office Action dated Aug. 29, 2018.
CN 201380060729.1 filed May 20, 2015 Office Action dated Feb. 6, 2018.
CN 201380060729.1 filed May 20, 2015 Office Action dated Jul. 26, 2017.
CN 201380060729.1 filed May 20, 2015 Office Action dated Mar. 14, 2019.
CN 201380060729.1 filed May 20, 2015 Office Action dated Nov. 4, 2016.
CN 201380060741.2 filed May 20, 2015 First Office Action dated May 3, 2016.
CN 201380060741.2 filed May 20, 2015 Office Action dated Aug. 9, 2017.
CN 201380060741.2 filed May 20, 2015 Office Action dated Dec. 19, 2016.
CN201280065776.0 filed Jul. 1, 2014, First Office Action dated Jun. 4, 2015.
CN201280065776.0 filed Jul. 1, 2014, Second Office Action dated Jan. 20, 2016.
EP 12159487.3 filed Mar. 14, 2012 Communication under Rule 71(3) dated Apr. 28, 2020.
EP 12159487.3 filed Mar. 14, 2012 Exam Report dated Jul. 31, 2014.
EP 12159487.3 filed Mar. 14, 2012 Office Action dated May 22, 2018.
EP 12159487.3 filed Mar. 14, 2012 Office Action dated Oct. 12, 2015.
EP 12159487.3 filed Mar. 14, 2012 Third Party Observations dated Dec. 2, 2016.
EP 12159487.3 filed Mar. 14, 2012 Third Party Observations dated Sep. 8, 2015.
EP 13856790.4 filed Apr. 28, 2015 Extended European Search Report dated Jul. 1, 2016.
EP 13856790.4 filed Apr. 28, 2015 Office Action dated Jul. 2, 2019.
EP 13856790.4 filed Apr. 28, 2015 Office Action dated Oct. 19, 2018.
EP 13857538.6 filed Apr. 29, 2015 Communication pursuant to Article 94(3) dated Apr. 30, 2020.
EP 13857538.6 filed Apr. 29, 2015 Extended European Search Report dated Jun. 17, 2016.
Ethomeen C/25 Information Sheet dated Jul. 28, 2005.
Johnson, James et al., "Activities of a Nitrofurazone-Containing Urinary Catheter and a Silver Hydrogel Catheter against Multidrug-Resistant Bacteria Characteristic of Catheter-Associated Urinary Tract Infection," Antimicrobial Agents and Chemotherapy, col. 43, No. 12, Dec. 1999, pp. 2990-2995.
JP 2015-543140 filed May 14, 2015 Notice of Allowance dated Feb. 22, 2018.
JP 2015-543140 filed May 14, 2015 Office Action dated Jul. 6, 2017.
JP 2015-543140 filed May 14, 2015 Office Action dated Oct. 18, 2017.
JP 2015-543141 filed May 19, 2015 Office Action dated Apr. 27, 2018.
JP 2015-543141 filed May 19, 2015 Office Action dated Aug. 10, 2017.
JP 2015-543141 filed May 19, 2015 Office Action dated Sep. 18, 2019.
Lubrizol Technical Data Sheet, Neutralizing Carbopol®* and Pemulen™ Polymers in Aqueous and Hydroalcoholic Systems, Sep. 16, 2009.
MX/a/2014/005144 filed Apr. 28, 2014 Office Action dated Jul. 14, 2016.
MX/a/2015/006058 filed May 13, 2015 Office Action dated May 25, 2018.
MX/a/2015/006059 filed May 13, 2015 Office Action dated Mar. 14, 2018.
Newman, Diane et al., "Review of Intermittent Catheterization and Current Best Practices," Urol Nurs. 2011:31(1).
PCT/US13/71046 filed Nov. 20, 2013 International Search Report and Written Opinion dated Feb. 21, 2014.
PCT/US13/71060 filed Nov. 20, 2013 International Search Report and Written Opinion dated Jan. 30, 2014.
PCT/US2012/068248 filed Dec. 6, 2012 International Preliminary Report on Patentability dated Jun. 10, 2014.
U.S. Appl. No. 11/104,388, filed Apr. 12, 2005 Notice of Allowance dated Mar. 21, 2014.
U.S. Appl. No. 13/047,175, filed Mar. 14, 2011 Decision on Appeal dated Feb. 28, 2017.
U.S. Appl. No. 13/047,175, filed Mar. 14, 2011 Examiner's Answer dated Nov. 4, 2014.
U.S. Appl. No. 13/047,175, filed Mar. 14, 2011 Final Office Action dated Mar. 17, 2014.
U.S. Appl. No. 13/682,406, filed Nov. 20, 2012 Decision on Appeal dated Jan. 29, 2018.
U.S. Appl. No. 13/682,406, filed Nov. 20, 2012 Examiner's Answer dated Aug. 11, 2016.
U.S. Appl. No. 13/682,406, filed Nov. 20, 2012 Final Office Action dated Jun. 5, 2015.
U.S. Appl. No. 13/682,406, filed Nov. 20, 2012 Non-Final Office Action dated Apr. 21, 2014.
U.S. Appl. No. 13/682,406, filed Nov. 20, 2012 Non-Final Office Action dated Nov. 28, 2014.
U.S. Appl. No. 13/682,420, filed Nov. 20, 2012 Decision on Appeal dated Jun. 16, 2017.
U.S. Appl. No. 13/682,420, filed Nov. 20, 2012 Examiner's Answer dated Apr. 8, 2015.
U.S. Appl. No. 16/790,404, dated Feb. 13, 2020 Non-Final Office Action dated Jul. 19, 2022.

* cited by examiner

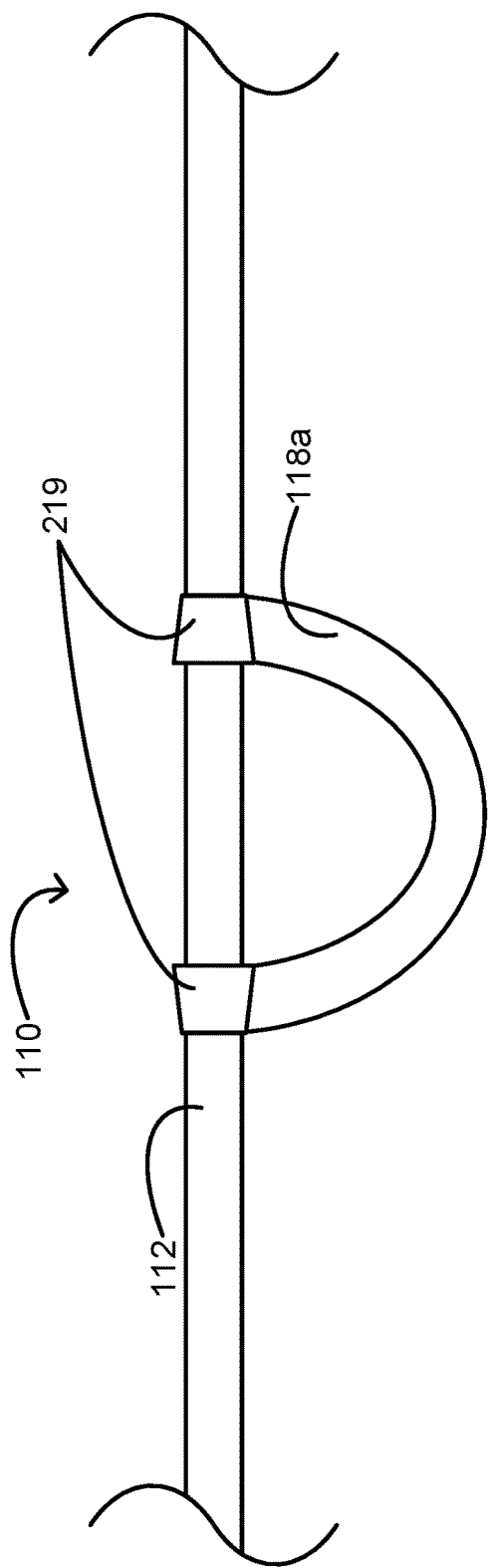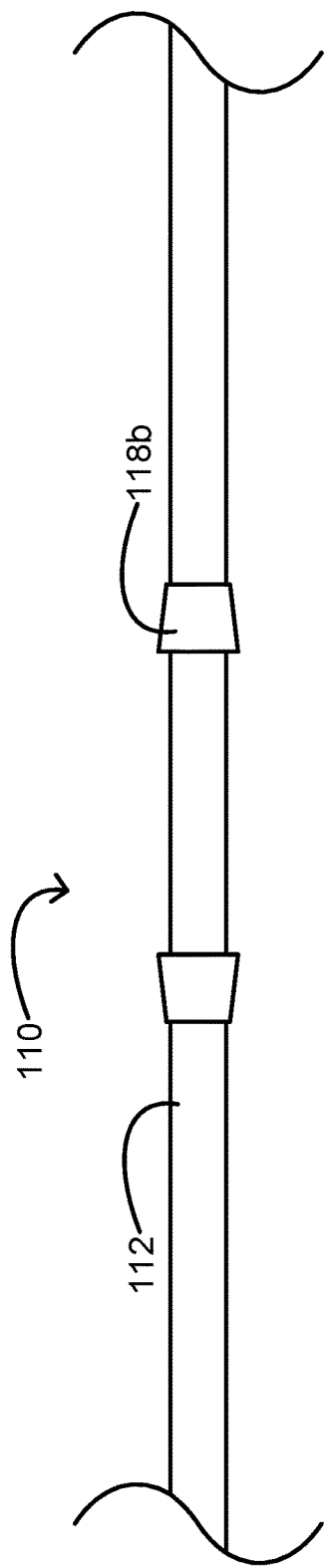
FIG. 2A
FIG. 2B

URINARY CATHETER BRIDGING DEVICE, SYSTEMS AND METHODS THEREOF

PRIORITY

This application is a U.S. national stage from International Application No. PCT/US2018/051550, filed Sep. 18, 2018, which claims the benefit of priority to U.S. Provisional Application No. 62/560,513, filed Sep. 19, 2017, each of which is incorporated by reference in its entirety into this application.

BACKGROUND

Current practice when preparing for use of a male external catheter ("MEC") is to pick up or pick out the MEC among several sizes, cleaning wipes, a drainage bag, and a securement device for the drainage bag. An MEC sizer helps with picking out the MEC, but an MEC sizer is commonly skipped, as it is not always available. The securement device is also not always available, and it, too, is commonly skipped. Making the current practice more potentially frustrating is variability in what advising clinicians can and do use. Non-standard use often creates problems with MECs such as leakage.

Furthermore, current practice when connecting an MEC to a drainage bag is for a user or patient to attach it directly to the sample port of the drainage bag. However, the sample port is designed to be connected to a flexible conduit like that of a Foley catheter. When MECs are placed directly on the sample port, they cannot be secured with an appropriate stabilization device (e.g., StatLock® catheter securement device). Rigidity and weight of the sample port and tubing can lead to problems such as leaks, disconnection, poor securement, discomfort, and the like.

Provided herein are urinary catheter devices, as well as systems and methods thereof that address the foregoing.

SUMMARY

Provided herein is bridging device including, in some embodiments, a piece of tubing including a securement feature such as a securement loop, a first connector at a first end of the piece of tubing, and a second connector at a second end of the piece of tubing. The securement loop is configured for securing the piece of tubing in a securement device. The first connector is configured to connect to an MEC. The second connector is configured to connect to a drainage bag for the MEC.

In some embodiments, the piece of tubing is of a sufficient length to maintain connections of the first connector to an MEC and the second connector to a drainage bag for the MEC under normal usage conditions for an MEC.

In some embodiments, the piece of tubing is about 12 inches.

In some embodiments, the securement loop alone is configured for securing the piece of tubing in a securement device.

In some embodiments, a portion of the piece of tubing encompassed by the securement loop alone is configured for securing the piece of tubing in a securement device.

In some embodiments, a portion of the piece of tubing encompassed by the securement loop and the securement loop together are configured for securing the piece of tubing in a securement device.

In some embodiments, the bridging device includes a visual indicator configured to indicate when a predetermined amount of time has elapsed since connecting the bridging device to an MEC and a drainage bag for the MEC.

In some embodiments, the visual indicator is configured for activation during one or more steps of a procedure for connecting the bridging device to an MEC and a drainage bag for the MEC.

In some embodiments, the predetermined amount of time is 12 hours.

In some embodiments, the first connector includes the visual indicator.

Also provided herein is a method including, in some embodiments, cutting from stock tubing a piece of tubing, fixing a first connector to a first end of the piece of tubing, and fixing a second connector to a second end of the piece of tubing. The first connector is configured to connect to an MEC, and the second connector is configured to connect to a drainage bag for the MEC, thereby forming a bridging device for fluidly connecting the MEC to the drainage bag.

In some embodiments, the stock tubing includes securement features at regular intervals along a span of the stock tubing. The piece of tubing cut from the stock tubing includes at least one securement feature of the securement features. In such embodiments, the at least one securement feature of the securement features is a securement loop or a pair of securement protrusions.

In some embodiments, the stock tubing does not include securement features along a span of the stock tubing. In such embodiments, the method further includes fixing a securement feature such as securement loop to the piece of tubing.

Also provided herein is an MEC kit including, in some embodiments, an MEC; a drainage bag for the MEC; and a bridging device for fluidly connecting the MEC to the drainage bag. The bridging device includes a piece of tubing including a securement feature such as securement loop, a first connector at a first end of the piece of tubing, and a second connector at a second end of the piece of tubing. The securement loop is configured for securing the bridging device in a securement device. The first connector is configured to connect to the MEC. The second connector is configured to connect to the drainage bag for the MEC.

In some embodiments, the MEC is one MEC of a selection of differently sized MECs in the MEC kit.

In some embodiments, the MEC kit further includes an MEC sizer configured for determining an appropriate MEC size for a user or patient.

In some embodiments, the MEC kit further includes the securement device.

In some embodiments, the securement loop alone is configured for securing the piece of tubing in the securement device.

In some embodiments, a portion of the piece of tubing encompassed by the securement loop alone is configured for securing the piece of tubing in the securement device.

In some embodiments, a portion of the piece of tubing encompassed by the securement loop and the securement loop together are configured for securing the piece of tubing in the securement device.

In some embodiments, the MEC kit further includes a wrap of a sterilizable material around contents of the MEC kit including at least the MEC, the drainage bag for the MEC, and the bridging device.

In some embodiments, the MEC kit further includes hand sanitizer and a cleansing kit outside the wrap configured for cleansing before MEC donning.

Also provided herein is a method including, in some embodiments, packing one or more compartments of a tray of an MEC kit, wrapping a sterilizable material around the tray; and sealing the tray in outer packaging to form the MEC kit. The one or more compartments are packed to include an MEC, a drainage bag for the MEC, and a bridging device for fluidly connecting the MEC to the drainage bag.

In some embodiments, the bridging device includes a piece of tubing including a securement feature such as a securement loop or securement protrusions, a first connector at a first end of the piece of tubing, and a second connector at a second end of the piece of tubing. The securement loop is configured for securing the bridging device in a securement device. The first connector is configured to connect to the MEC. The second connector is configured to connect to the drainage bag for the MEC.

These and other features of the concepts provided herein may be better understood with reference to the drawings, description, and appended claims.

DRAWINGS

FIG. 1 provides a schematic illustrating a urinary catheter system including a bridging device in accordance with some embodiments.

FIG. 2A provides a schematic illustrating a first securement feature of a bridging device in accordance with some embodiments.

FIG. 2B provides a schematic illustrating a second securement feature in accordance with some embodiments.

Figure 3A:
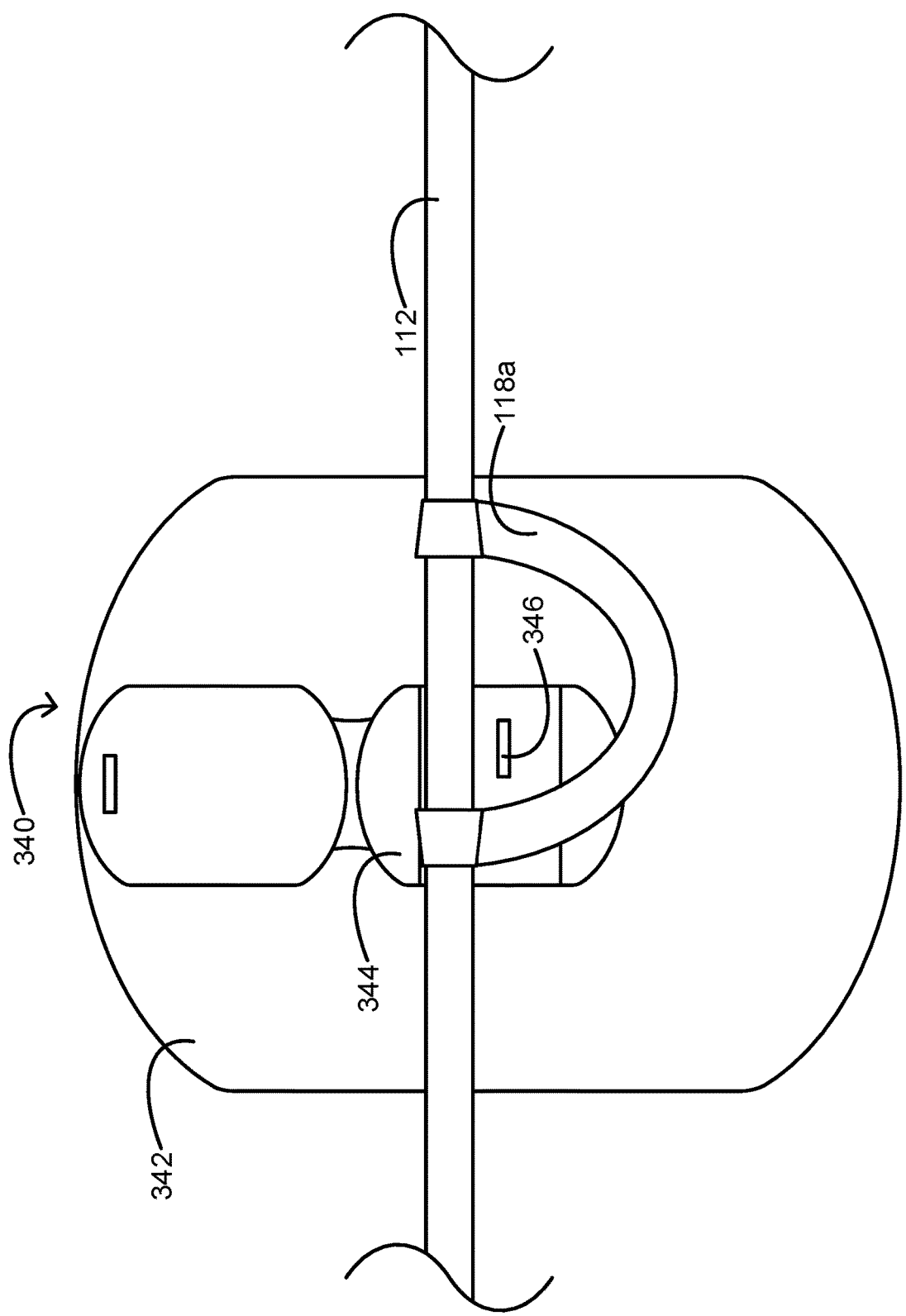

FIG. 3A provides a schematic illustrating a securement loop over a securement device in accordance with some embodiments.

Figure 3B:
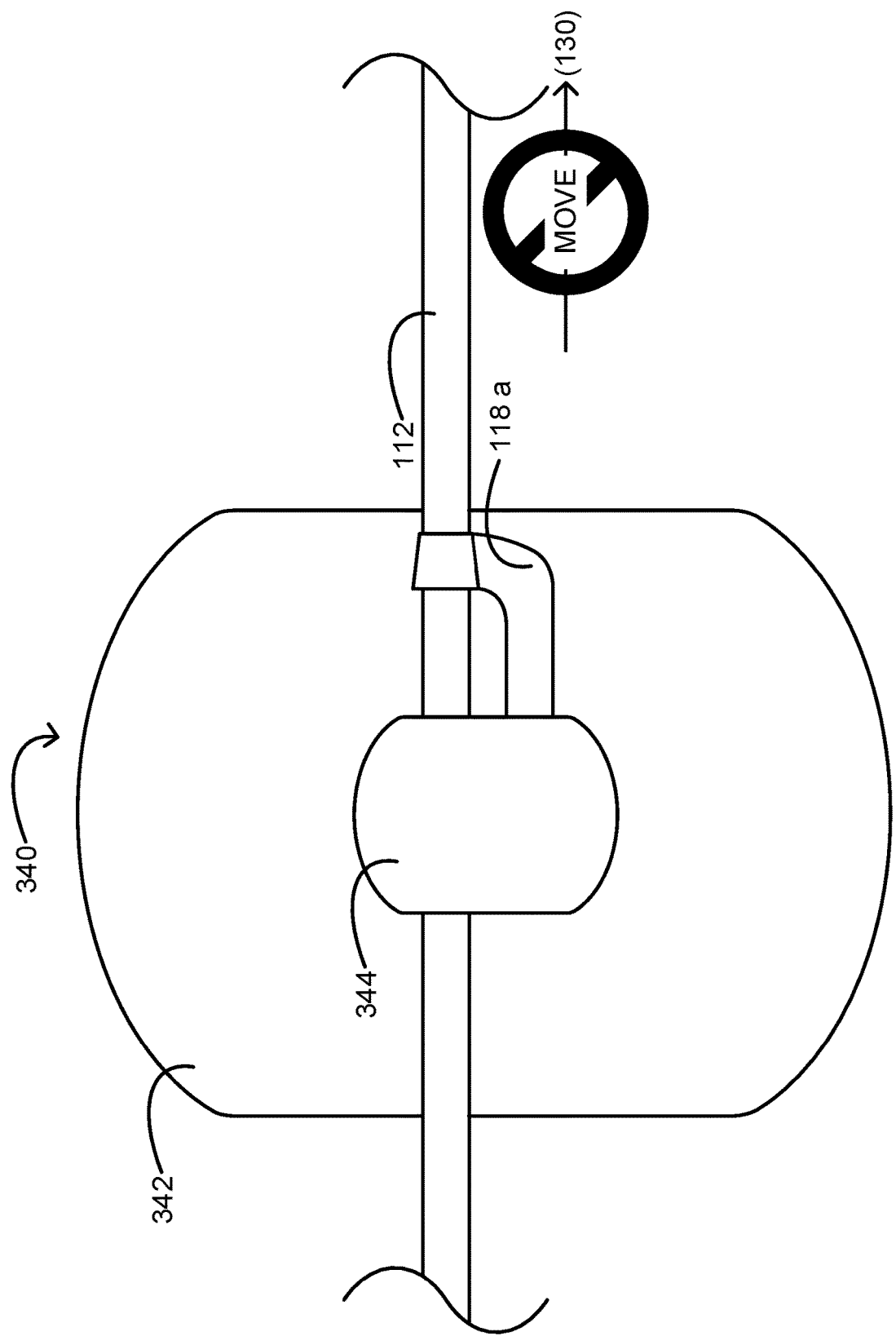

FIG. 3B provides a schematic illustrating a securement loop locked in a securement device in accordance with some embodiments.

Figure 4:
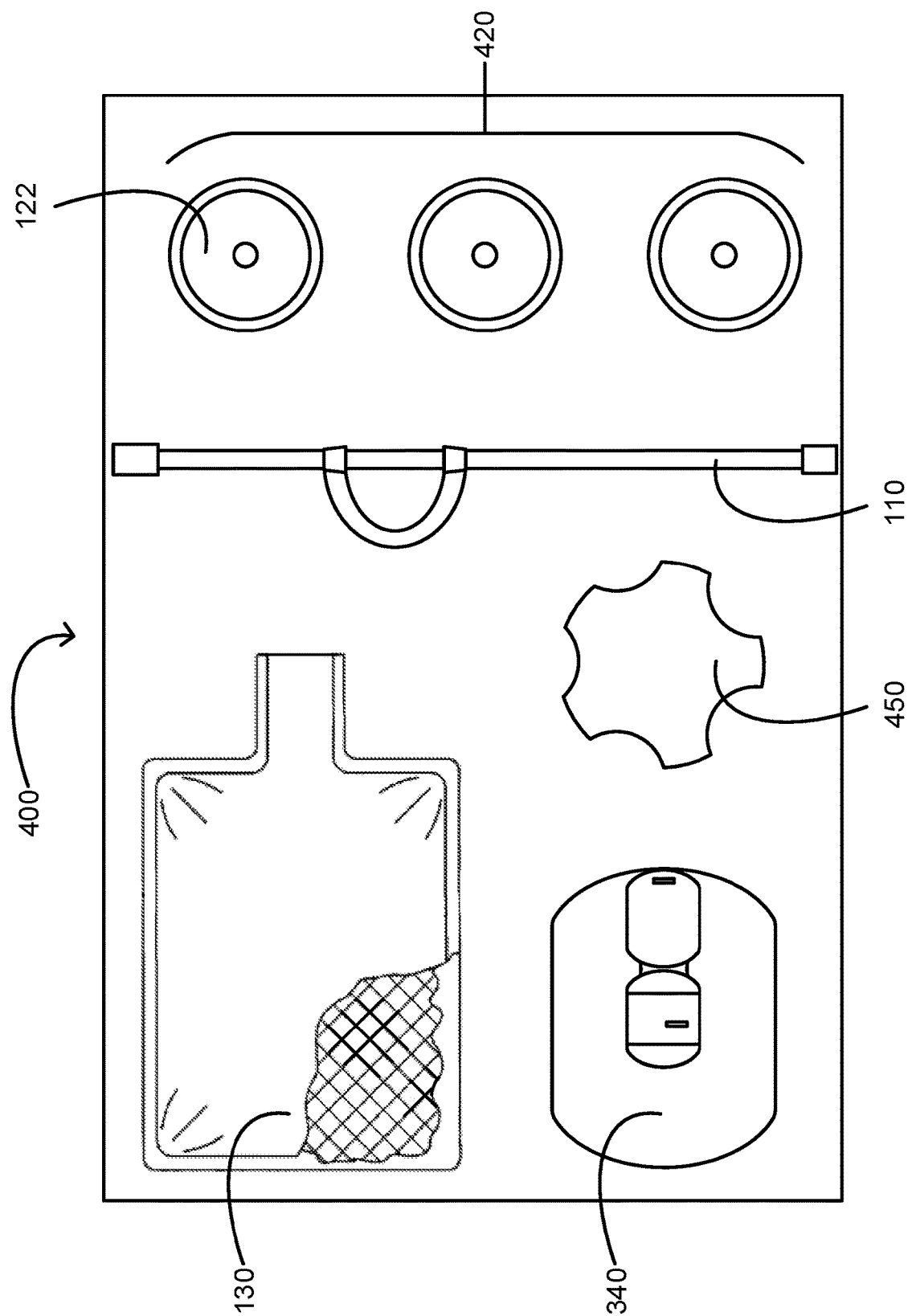

FIG. 4 provides a schematic illustrating an MEC kit or a portion thereof in accordance with some embodiments.

DESCRIPTION

Before some particular embodiments are provided in greater detail, it should be understood that the particular embodiments provided herein do not limit the scope of the concepts provided herein. It should also be understood that a particular embodiment provided herein can have features that can be readily separated from the particular embodiment and optionally combined with or substituted for features of any of a number of other embodiments provided herein.

Regarding terminology used herein, it should also be understood the terminology is for the purpose of describing some particular embodiments, and the terminology does not limit the scope of the concepts provided herein. Unless indicated otherwise, ordinal numbers (e.g., first, second, third, etc.) are used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

With respect to "proximal," a "proximal portion" or a "proximal end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Current practice when preparing for use of a male external catheter ("MEC") is to pick up or pick out the MEC among several sizes, cleaning wipes, a drainage bag, and a securement device for the drainage bag. An MEC sizer helps with picking out the MEC, but an MEC sizer is commonly skipped, as it is not always available. The securement device is also not always available, and it, too, is commonly skipped. Making the current practice more potentially frustrating is variability in what advising clinicians can and do use. Non-standard use often creates problems with MECs such as leakage.

Furthermore, current practice when connecting an MEC to a drainage bag is for a user or patient to attach it directly to the sample port of the drainage bag. However, the sample port is designed to be connected to a flexible conduit like that of a Foley catheter. When MECs are place directly on the sample port, they cannot be secured with an appropriate stabilization device (e.g., StatLock®). Rigidity and weight of the sample port and tubing can lead to problems such as leaks, disconnection, poor securement, discomfort, and the like.

Provided herein are urinary catheter devices, as well as systems and methods thereof that address the foregoing.

Referring now to FIG. 1, a schematic is provided illustrating a urinary catheter system 100 including a bridging device 110 in accordance with some embodiments. As shown, the urinary catheter system 100 includes an MEC 122, a drainage bag 130 for the MEC 122, and the bridging device 110 configured for fluidly connecting the MEC 122 to the drainage bag 130.

The bridging device 110 includes a piece of tubing 112 including a securement feature 118 such as a securement loop (shown), a first connector 114 at a first end of the piece of tubing 112, and a second connector 116 at a second end of the piece of tubing 112. The securement feature 118 is configured for securing the bridging device 110 in a securement device. The first connector 114 is configured to connect to the MEC 122. The second connector 116 is configured to connect to the drainage bag 130 for the MEC 122.

The piece of tubing 112 is a piece of medical grade tubing formed from a biocompatible polymer such as, but not limited to, silicone, polyurethane, polyvinyl chloride ("PVC"), low-density polyethylene ("LDPE"), or combinations thereof such as co-polymers or polymer blends. The piece of tubing 112 is configured for user comfort. As such, the piece of tubing 112 is soft and flexible. According to one embodiment, the piece of tubing 112 is without plasticizers such as diethylhexyl phthalate ("DEHP").

The piece of tubing 112 is of a sufficient length to maintain connections of the first connector 114 to an MEC and the second connector 116 to a drainage bag for the MEC under normal usage conditions for an MEC such as those indicated in instructions for use of a urinary catheter system such as the urinary catheter system 100. The length of the piece of tubing 112 keeps the weight of the tubing and any contents thereof from tugging on and disconnecting from an MEC. The piece of tubing can have a length of at least about 3 inches, 4 inches, 5 inches, 6 inches, 7 inches, 8 inches, 9 inches, 10 inches, 11 inches, or 12 inches. Alternatively, the piece of tubing can have a length of no more than about 12 inches, 11 inches, 10 inches, 9 inches, 8 inches, 7 inches, 6 inches, 5 inches, 4 inches, or 3 inches. As such, the piece of tubing can have a length of at least 3 inches and no more than 12 inches, including a length of at least 6 inches and no more than 12 inches, such as a length of at least 9 inches and no more than 12 inches, or, for example, a length of at least 10 inches and no more than 12 inches. Different lengths for different pieces of tubing are used to accommodate men of different heights or preferences with respect to drainage bag placement (e.g., upper leg or thigh, lower leg or ankle, etc.).

The bridging device 110 further includes, in some embodiments, a visual indicator configured to indicate when a predetermined amount of time has elapsed since connecting the bridging device 110 to an MEC, a drainage bag for the MEC, or both. This is useful for reminding a user or patient to replace the MEC after the predetermined amount of time has elapsed. The predetermined amount of time can be at least 4 hours, 8 hours, 12 hours, 16 hours, 20 hours, or 24 hours. The predetermined amount of time can be no more than 24 hours, 20 hours, 16 hours, 12 hours, 8 hours, or 4 hours. As such, the predetermined amount of time can be at least 4 hours and no more than 24 hours, including at least 8 hours and no more than 20 hours, such as at least 8 hours and no more than 16 hours, or, for example, about 12 hours.

The visual indicator is configured for activation and, thereby, starting the predetermined amount of time during one or more steps of a procedure for connecting the bridging device 110 to an MEC, a drainage bag for the MEC, or both. Activation can include, but is not limited to, peeling an adhered backing off a component of the bridging device 110 or breaking a fluid-filled blister on a component to start a process of chemical migration, chemical reaction, or a combination thereof resulting in a discernable visual endpoint indicating the predetermined amount of time has elapsed. For example, the first connector 114 of the bridging device 110 can include the visual indicator. Subsequent to activation of the visual indicator prior to or at the time of connecting the first connector 114 to an MEC, the visual indicator will change color after the predetermined amount of time has elapsed reminding the user or patient to replace the MEC.

The bridging device 110 includes the first connector 114 at the first end of the piece of tubing 112 configured to connect to an MEC, and the bridging device 110 includes the second connector 116 at the second end of the piece of tubing 112 configured to connect to a drainage bag for the MEC. Each of the first connector 114 and the second connector 116 can be formed from a biocompatible polymer such as, but not limited to, silicone, polyurethane, PVC, LDPE, or combinations thereof such as co-polymers or polymer blends optionally without plasticizers such as DEHP. Such connecters can be bonded or welded over the piece of tubing 112 using heat, ultrasound, solvent, or adhesive as appropriate for bonding or welding.

While FIG. 1 shows the first connector 114 and the second connector 116 as block forms, each of the first connector 114 and the second connector 116 can be shaped as needed for respectively connecting to the MEC 122 and the drainage bag 130 for the MEC 122. For example, the first connector 114 can be tapered from an outer diameter larger than that of the piece of tubing 112 to an outer diameter commensurate with or smaller than an inner diameter of a tip of an MEC. Likewise, the second connector 116 can be tapered from an outer diameter larger than that of the piece of tubing 112 to an outer diameter commensurate with or smaller than a port of a drainage bag. If an intermediate portion of tubing is already connected to a manufactured drainage bag, the second connector 116 need not be tapered as the second connector 116 can be placed over the intermediate portion of tubing like the piece of tubing 112. However, in other embodiments, the second connector 116 can be tapered from an outer diameter larger than that of the piece of tubing 112 to an outer diameter commensurate with or smaller than an inner diameter of the intermediate portion of tubing.

Referring now to FIGS. 2A and 2B, schematics are provided respectively illustrating a first securement feature 118a (e.g., a securement loop 118a) and a second securement feature 118b (e.g., securement protrusions 118b) of the bridging device 110 in accordance with some embodiments. As shown, the securement feature 118 of the bridging device 110 can include, but is not limited to the securement loop 118a or the securement protrusions 118b. The securement feature 118 (e.g., the securement protrusions 118b) can be formed (e.g., molded, extruded, etc.) with the piece of tubing 112 and, thereby, integral with the piece of tubing 112. Alternatively, the securement feature 118 can be removably or fixedly attached to the piece of tubing 112. For example, the securement loop 118a can include terminal rings 219, each ring thereof including an inner diameter commensurate with or larger than the outer diameter of the piece of tubing 112. The piece of tubing 112 can be disposed through the rings 219 to removably attach the securement loop 118a to the piece of tubing 112. The rings 219 of the securement loop 118a can be bonded or welded as set forth herein to fixedly attached the securement feature 118a to the piece of tubing 112. However, with rings 219 including an inner diameter commensurate with the outer diameter of the piece of tubing 112, interference or friction between the rings 219 and the piece of tubing 112 keep the securement loop 118a localized on the piece of tubing 112.

Referring now to FIGS. 3A and 3B, schematics are provided illustrating the piece of tubing 112 and the securement loop 118a of the bridging device 110 respectively placed over a securement device 340 (FIG. 3A) and locked in the securement device 340 (FIG. 3B) in accordance with some embodiments. As shown, the securement device 340 includes at least an adhesive-backed anchor pad 342 and a lidded retainer 344. Securement devices such as the securement device 340 of FIGS. 3A and 3B can further include a post 346 in a base of the retainer 344 defining two channels for securing the bridging device 110 with the securement loop 118a. Of the two channels, a first channel can be wider than a second channel, thereby configuring the first channel to hold the piece of tubing 112 (wider) and the second channel to hold the securement loop 118a (narrower).

Securement devices need not include the post 346 in the base of the retainer 344 for securing bridging devices. For example, the post 346 in the base of the retainer 344 of the securement device 340 is not needed for the bridging device 110 with the securement protrusions 118b, which securement protrusions 118b restrict longitudinal movement of the piece of tubing 112 through the retainer 344 when the lid thereof is closed. That being said, the securement device 340 of FIGS. 3A and 3B provides a configuration of the retainer 344 that can be used in different ways for any one or more bridging devices like the bridging device 110. With respect to the bridging device 110 having the securement loop 118a, for example, the securement loop 118a alone can be used to secure the bridging device 110 in the securement device 340. The securement loop 118a can be locked in either one of the two channels. Alternatively, a portion of the piece of tubing 112 encompassed by the securement loop 118a alone can be used to secure the bridging device 110 in the securement device 340. The portion of the piece of tubing 112 can be locked in the wider channel of the two channels. Likewise, the bridging device 110 having the securement protrusions 118b can be secured between the securement protrusions 118b. However, for at least the bridging device 110 having the securement loop 118a, optimum results result when the portion of the piece of tubing 112 encompassed by the securement loop 118a and the securement loop 118a together are secured in the two channels around the post 346.

Referring now to FIG. 4, a schematic is provided illustrating an MEC kit 400 or a portion thereof in accordance with some embodiments. As shown, the MEC kit 400 includes MEC-related contents including a selection of MECs 420 such as the MEC 122; a drainage bag for the MECs 420 such as the drainage bag 130; and a bridging device such as the bridging device 110 for fluidly connecting an MEC of the MECs 420 to the drainage bag 130. The MEC-related items can be placed in one or more compartments of a tray or in one or more pockets of a wrap assembly.

The selection of MECs 420 includes a selection of different types of MECs, a selection of differently sized MECs, or a combination thereof. For example, the selection of MECs 420 includes a selection of the most common sizes of MECs of a single type of MEC. The MEC kit 400 can further include an MEC sizer or MEC sizing wheel 450 configured for determining an appropriate MEC size for a user or patient.

As set forth herein, the bridging device 110 includes the piece of tubing 112 including a securement feature 118 such as the securement loop 118a of the bridging device 110 shown in the MEC kit 400 of FIG. 4. The securement loop 118a is configured for securing the bridging device 110 in a securement device such as the securement device 340, which is included in the MEC kit 400 in some embodiments. In such embodiments, the securement device can be a StatLock® Foley stabilization device (C. R. Bard, Inc., Murray Hill, N.J., USA) or the like. Alcohol preps, skin protectant pads, and the like for preparing a user or patient for adhering the securement device 340 can also be included in the MEC kit 400.

An MEC package including the MEC kit 400 includes a wrap of a sterilizable material (e.g., central supply room ["CSR"] wrap) around the contents of the MEC kit 400 including the selection of MECs 420, the drainage bag 130, and the bridging device 110. If such contents are in one or more compartments of a tray, the sterilizable material can be wrapped around the tray. If such contents are in one or more pockets of a wrap assembly, the wrap assembly including any pockets can be made of the sterilizable material. Such a wrap assembly can be rolled up around the contents of the MEC kit 400. The MEC package can further include hand sanitizer and a cleansing kit outside the sterilizable wrap but sealed within an outer packaging of the MEC package. The hand sanitizer and cleansing kit are configured for user or patient cleansing before MEC donning.

Methods

The bridging device 110 can be formed by cutting from stock tubing the piece of tubing 112, fixing the first connector 114 to the first end of the piece of tubing 112, and fixing the second connector 116 to the second end of the piece of tubing 112. The stock tubing can include securement features (e.g., the securement loop 118a, the securement protrusions 118b) at regular intervals along a span of the stock tubing. The piece of tubing 112 cut from such stock tubing includes at least one securement feature 118 of the securement features. In such embodiments, the at least one securement feature 118 of the securement features is the securement loop 118a or the pair of securement protrusions 118b. Alternatively, the stock tubing does not include securement features along any span of the stock tubing. The piece of tubing 112 cut from such stock tubing lacks any securement features. In such embodiments, the securement features are removably or fixedly attached to the piece of tubing 112 as set forth herein.

The MEC package including the MEC kit 400 can be formed by packing one or more compartments of a tray or one more pockets of a wrap assembly of the MEC kit with the MEC-related contents set forth herein including, but not limited to, the selection of MECs 420, the drainage bag 130, and the bridging device 110. If the MEC kit 400 includes the tray, a sterilizable material can be wrapped around the tray including the contents. If the MEC kit 400 includes the wrap assembly, itself a sterilizable material, the wrap assembly can be rolled up around the contents of the MEC kit 400. The tray or the wrap assembly is disposed in the outer packaging; the hand sanitizer and the cleansing kit are disposed in the outer packaging but outside the sterilizable material around the tray or of the wrap assembly; the contents of the outer packaging are sterilized (e.g. sterilized with a sterilizable gas) within the outer packaging; and the MEC package is sealed.

In view of the foregoing, embodiments of a bridging device 110 are provided to fluidly connect an MEC such as the MEC 122 and a sample port of a drainage bag such as the drainage bag 130 to allow for easier and more flexible movement of the MEC 122 while draining urine towards the sample port and any intermediate PVC tubing. The bridging device 110 includes a section that allows for securement via, for example, an appropriate StatLock® device with a securement feature such as the securement loop 118a that prevents pistoning while secured. The bridging device 110 also has an indicator that, when connected to the MEC 122, will change color after a period of time (e.g., 12 hours) to indicate it is time to replace the MEC.

The bridging device 110 serves as a flexible bridge between the MEC 122 and the sample port of the drainage bag 130 to alleviate certain problems such as those set forth herein. The length of the bridging device 110 (e.g., 12 inches) allows for the sample port to be placed farther away from the patient without dislodging the MEC 122, and the length of the bridging device 110 keeps the weight of the tubing from tugging on the MEC 122. The securement loop 118a allows the bridging device 110 to be connected to a StatLock® stabilization device around the bifurcation holder or retainer thereof such that the bridging device 110 does not slide back and forth (i.e., piston) while allowing the StatLock® device to swivel. Again, the end of the bridging device 110 that connects to the MEC 122 can have an indicator on it such that when both the bridging device 110 and MEC 122 are connected together, the color will change after about 12 hours to serve as a reminder to replace the MEC 122.

Further in view of the foregoing, embodiments of an MEC kit 400 include MEC-related contents for MEC usage in one easy-to-use kit. A selection of MECs (e.g., 3 MECs) are included inside the MEC kit 400 to make available the most commonly used MEC sizes. Other contents include large precleaning wipes, a StatLock® stabilization device, the bridging device 110, and the MEC sizer 450.

The MEC kit 400 alleviates certain frustrations such as those set forth herein, and the MEC kit 400 combines best practices for MEC usage. The MEC kit 400 also standardizes MEC practice by having clinicians use a standard set of MEC-related components, as well as standardized directions for easier training and better competency with nurses. The MEC kit 400 can include a set of wipes outside the CSR wrap to preclean a patient's groin area (allowing for the MEC adhesive to stick properly). Inside the MEC kit 400 is the bridging device 110 that connects an MEC to, for example, a Foley kit. The selection of MECs 420 allows a nurse to choose the best size of MEC without having to leave the MEC kit 400. The MECs 420 present in the MEC kit 400 are not separately sealed in packaging. As such, a clinician cannot save potentially contaminated MECs for later use. Extra MECs are to be discarded with the packaging of the MEC kit 400 as a safety measure. Labels inside the MEC kit 400 guide the clinician in each step of the MEC placement process, and short explanations provide instructions to clinicians on what the bridging device 110 does.

While some particular embodiments have been provided herein, and while the particular embodiments have been provided in some detail, it is not the intention for the particular embodiments to limit the scope of the concepts presented herein. Additional adaptations and/or modifications can appear to those of ordinary skill in the art, and, in broader aspects, these adaptations and/or modifications are encompassed as well. Accordingly, departures may be made from the particular embodiments provided herein without departing from the scope of the concepts provided herein.

What is claimed is:

1. A bridging device, comprising:
    a piece of flexible tubing including a securement loop directly attached to the piece of tubing, the securement loop configured for securing the piece of tubing in a securement device;
    a first connector at a first end of the piece of tubing, the first connector configured to connect to a male external catheter ("MEC"); and
    a second connector at a second end of the piece of tubing, the second connector configured to connect to a drainage bag for the MEC.

2. The bridging device of claim 1, wherein the piece of tubing is of a sufficient length to maintain connections of the first connector to the MEC and the second connector to the drainage bag for the MEC under normal usage conditions for the MEC.

3. The bridging device of claim 1, wherein the securement loop alone is configured for securing the piece of tubing in a securement device.

4. The bridging device of claim 1, wherein a portion of the piece of tubing encompassed by the securement loop alone is configured for securing the piece of tubing in a securement device.

5. The bridging device of claim 1, wherein a portion of the piece of tubing encompassed by the securement loop and the securement loop together are configured for securing the piece of tubing in a securement device.

6. The bridging device of claim 1, wherein the securement loop is configured to be locked within the securement device to restrict longitudinal movement of the piece of flexible tubing.

7. The bridging device of claim 1, wherein the bridging device includes a visual indicator configured to indicate when a predetermined amount of time has elapsed since connecting the bridging device to the MEC and the drainage bag for the MEC.

8. The bridging device of claim 7, wherein the predetermined amount of time is 12 hours.

9. The bridging device of claim 7, wherein the visual indicator is a discernable visual endpoint of a chemical migration or a chemical reaction.

10. The bridging device of claim 9, wherein the visual indicator is configured for activation during one or more steps of a procedure for connecting the bridging device to the MEC and the drainage bag for the MEC, the one or more steps of the procedure including peeling an adhered backing off a component of the bridging device or breaking a fluid-filled blister on a component to start the chemical migration or the chemical reaction.

11. The bridging device of claim 9, wherein the first connector includes the visual indicator.

12. A male external catheter ("MEC") kit, comprising:
    an MEC;
    a drainage bag for the MEC; and
    a bridging device including:
        a piece of flexible tubing including a securement loop directly attached to the piece of tubing, the securement loop configured for securing the bridging device in a securement device;
        a first connector at a first end of the piece of tubing, the first connector configured to connect to the MEC; and
        a second connector at a second end of the piece of tubing, the second connector configured to connect to the drainage bag for the MEC.

13. The MEC kit of claim 12, wherein the MEC is one MEC of a selection of differently sized MECs in the MEC kit.

14. The MEC kit of claim 12, further comprising:
    an MEC sizer configured for determining an appropriate MEC size for a user or patient; and
    the securement device.

15. The MEC kit of claim 14, wherein the securement loop alone is configured for securing the piece of tubing in the securement device.

16. The MEC kit of claim 14, wherein a portion of the piece of tubing encompassed by the securement loop alone is configured for securing the piece of tubing in the securement device.

17. The MEC kit of claim 14, wherein a portion of the piece of tubing encompassed by the securement loop and the securement loop together are configured for securing the piece of tubing in the securement device.

18. The MEC kit of claim 12, further comprising a wrap of a sterilizable material around contents of the MEC kit including at least the MEC, the drainage bag for the MEC, and the bridging device.

19. The MEC kit of claim 18, further comprising hand sanitizer and a cleansing kit outside the wrap configured for cleansing before MEC donning.

20. A method, comprising:
packing one or more compartments of a tray of a male external catheter ("MEC") kit with an MEC, a drainage bag for the MEC, and a bridging device for fluidly connecting the MEC to the drainage bag, the bridging device including:
- a piece of flexible tubing including a securement loop directly attached to the piece of tubing, the securement loop configured for securing the piece of tubing in a securement device;
- a first connector at a first end of the piece of tubing, the first connector configured to connect to the MEC; and
- a second connector at a second end of the piece of tubing, the second connector configured to connect to the drainage bag;

wrapping a sterilizable material around the tray; and
sealing the tray in outer packaging to form the MEC kit.

* * * * *